(12) United States Patent
Yen

(10) Patent No.: US 9,929,351 B2
(45) Date of Patent: Mar. 27, 2018

(54) INDENOTRIPHENYLENE-BASED AMINE DERIVATIVE FOR ORGANIC ELECTROLUMINESCENT DEVICE

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 219 days.

(21) Appl. No.: 14/988,765

(22) Filed: Jan. 6, 2016

(65) Prior Publication Data

US 2016/0240784 A1    Aug. 18, 2016

Related U.S. Application Data

(63) Continuation-in-part of application No. 14/623,508, filed on Feb. 17, 2015.

(51) Int. Cl.

| | |
|---|---|
| *H01L 51/00* | (2006.01) |
| *C07C 211/61* | (2006.01) |
| *C07C 211/54* | (2006.01) |
| *C07D 209/86* | (2006.01) |
| *C07D 307/91* | (2006.01) |
| *H01L 51/50* | (2006.01) |

(52) U.S. Cl.
CPC .......... *H01L 51/006* (2013.01); *C07C 211/54* (2013.01); *C07C 211/61* (2013.01); *C07D 209/86* (2013.01); *C07D 307/91* (2013.01); *H01L 51/0052* (2013.01); *H01L 51/0056* (2013.01); *H01L 51/0057* (2013.01); *H01L 51/0058* (2013.01); *H01L 51/0059* (2013.01); *H01L 51/0061* (2013.01); *H01L 51/0072* (2013.01); *H01L 51/0073* (2013.01); *C07C 2603/14* (2017.05); *C07C 2603/54* (2017.05); *C07C 2603/94* (2017.05); *H01L 51/5056* (2013.01); *H01L 51/5096* (2013.01)

(58) Field of Classification Search
CPC ............... H01L 51/006; H01L 51/0058; H01L 51/0059; H01L 51/0072; H01L 51/0073; H01L 51/0057; H01L 51/0056; H01L 51/0052; H01L 51/0061; H01L 51/5096; H01L 51/5056; C07D 209/86; C07D 307/91; C07C 211/61; C07C 211/54; C07C 2603/14; C07C 2603/09

See application file for complete search history.

(56) References Cited

U.S. PATENT DOCUMENTS

| | | | |
|---|---|---|---|
| 8,962,160 | B2 | 2/2015 | Yen et al. |
| 8,993,130 | B2 | 3/2015 | Yen et al. |
| 9,048,437 | B2 | 6/2015 | Yen et al. |
| 2013/0048975 | A1 | 2/2013 | Hong et al. |
| 2014/0151645 | A1 | 6/2014 | Yen et al. |

FOREIGN PATENT DOCUMENTS

| | | |
|---|---|---|
| WO | 2008062636 A1 | 5/2008 |
| WO | 2012091471 A2 | 7/2012 |

*Primary Examiner* — Alexander Kollias

(57) ABSTRACT

The present invention discloses a indenotriphenylene-based amine derivative is represented by the following formula (I), the organic EL device employing the derivative as hole transport material, electron blocking material, can increasing efficiency and half-life time.

formula (I)

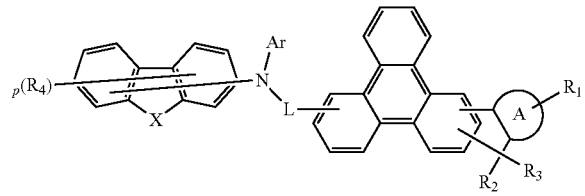

wherein $R_1$ to $R_4$, p, X, A ring, L and Ar are the same definition as described in the present invention.

8 Claims, 1 Drawing Sheet

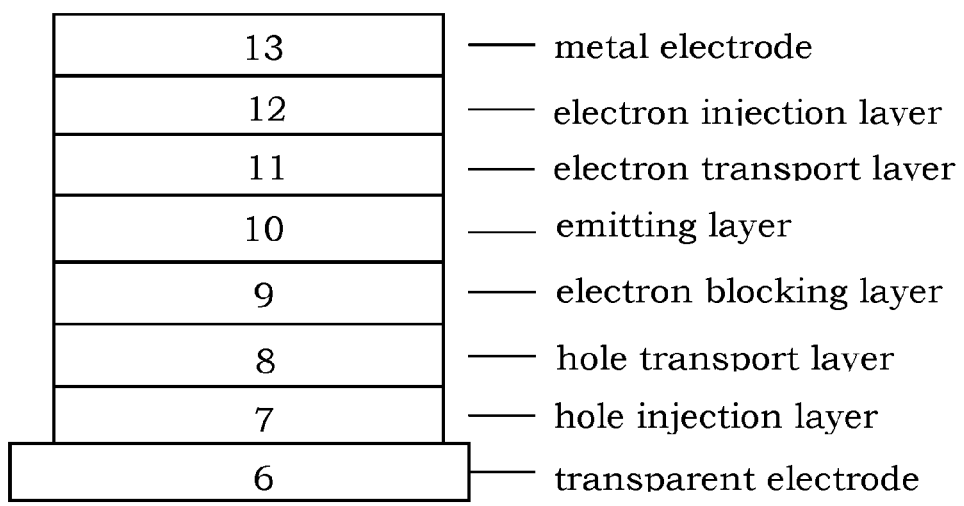

INDENOTRIPHENYLENE-BASED AMINE DERIVATIVE FOR ORGANIC ELECTROLUMINESCENT DEVICE

This application is a Continuation-in-Part of U.S. patent Ser. No. 14/623,508, filed Feb. 17, 2015.

FIELD OF INVENTION

The present invention generally relates to a indenotriphenylene-based amine derivative and organic electroluminescent (herein referred to as organic EL) device using the derivative. More specifically, the present invention relates to the derivative having general formula (I), an organic EL device employing the derivative as hole transport material (HTM) and/or electron blocking material (EBM) can efficiently increase the efficiency and half-life time.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

There continues to be a need for organic EL materials which is able to efficiently transport electrons or holes and block electrons or holes, with good thermal stability, and more efficient hole transport material (HTM) and electron blocking material (EBM) that can lower driving voltage and power consumption, increasing efficiency and half-life time. According to the reasons described above, the present invention has the objective of resolving such problems of the prior-art like as EP2313362A1, US20130048975A1, WO20080672636A1, WO2012091471A2. In the present invention we used diarylamine group linked to the position 5, 6, 7 and 8 of indenotriphenylene core and offering a light emitting device which is excellent in its thermal stability, high luminance efficiency, high luminance and long half-life time to improve the prior materials and the prior organic EL device.

SUMMARY OF THE INVENTION

Provided a indenotriphenylene-based amine derivative can use as hole transport material, electron blocking material for organic EL device. The derivative can overcome the drawbacks of the prior materials such as EP2313362A1, US20130048975A1, WO20080672636A1, WO2012091471A2, like as lower efficiency, half-life time and higher power consumption.

An object of the present invention is to provide the indenotriphenylene-based amine derivative which can be used as hole transport layer, electron blocking layer for organic EL device.

The present invention has the economic advantages for industrial practice. Accordingly the present invention, the indenotriphenylene-based amine derivative which can be used as hole transport material, electron blocking material for organic EL device is disclosed. The mentioned the indenotriphenylene-based amine derivative is represented by the following formula (I)

formula (I)

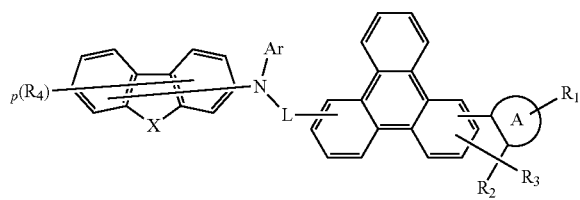

wherein A ring represents a phenyl group and fused ring hydrocarbon units with two to four rings group, L represents a single bond or a substituted or unsubstituted divalent arylene group having 6 to 30 ring carbon atoms, p represents an integer of 0 to 7, X represents a divalent bridge selected from the atom or group consisting from O, S, C($R_5$)($R_6$) and $NR_7$ or represents non-bridge and to form as a substituted or unsubstituted biphenyl group; Ar is selected from the group consisting of a substituted or unsubstituted aryl group having 6 to 50 carbon atoms, a substituted or unsubstituted heteroaryl group having 3 to 50 carbon atoms, $R_1$ to $R_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is electron transport layer which is deposited onto 10, 12 is electron injection layer which is deposited on to 11.

DESCRIPTION OF THE PREFERRED EMBODIMENTS

What probed into the invention is the indenotriphenylene-based amine derivative and organic EL device using the indenotriphenylene-based amine derivative. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the indenotriphenylene-based amine derivative which can be used as hole transport material, electron blocking material for organic EL device are disclosed. The mentioned derivative is represented by the following formula (I):

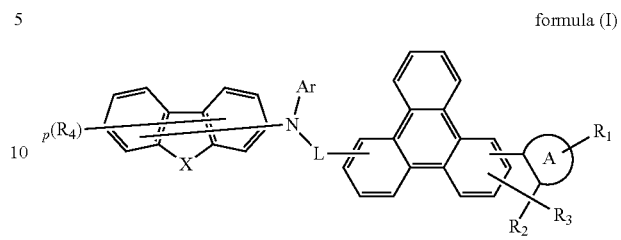

formula (I)

wherein A ring represents a phenyl group and fused ring hydrocarbon units with two to four rings group, L represents a single bond or a substituted or unsubstituted divalent arylene group having 6 to 30 ring carbon atoms, p represents an integer of 0 to 7, X represents a divalent bridge selected from the atom or group consisting from O, S, C($R_5$)($R_6$) and $NR_7$ or represents non-bridge and to form as a substituted or unsubstituted biphenyl group; Ar is selected from the group consisting of a substituted or unsubstituted aryl group having 6 to 50 carbon atoms, a substituted or unsubstituted heteroaryl group having 3 to 50 carbon atoms, $R_1$ to $R_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

According to the above-mentioned formula (I) wherein L is represented the following formulas:

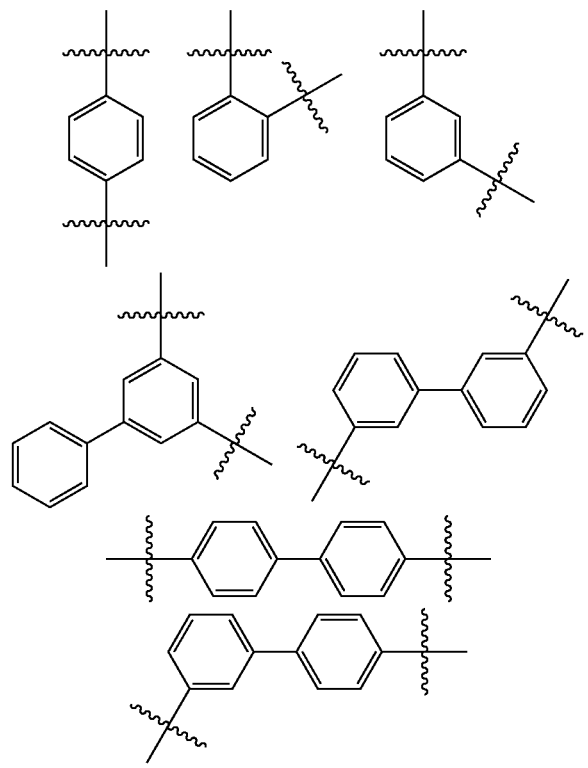

According to the above-mentioned formula (I) wherein A ring is consisting of naphthyl group, anthracenyl group, phenanthrenyl group, pyrenyl group, chrysenyl group and triphenylene group.
According to the above-mentioned formula (I) wherein Ar is represented the following:
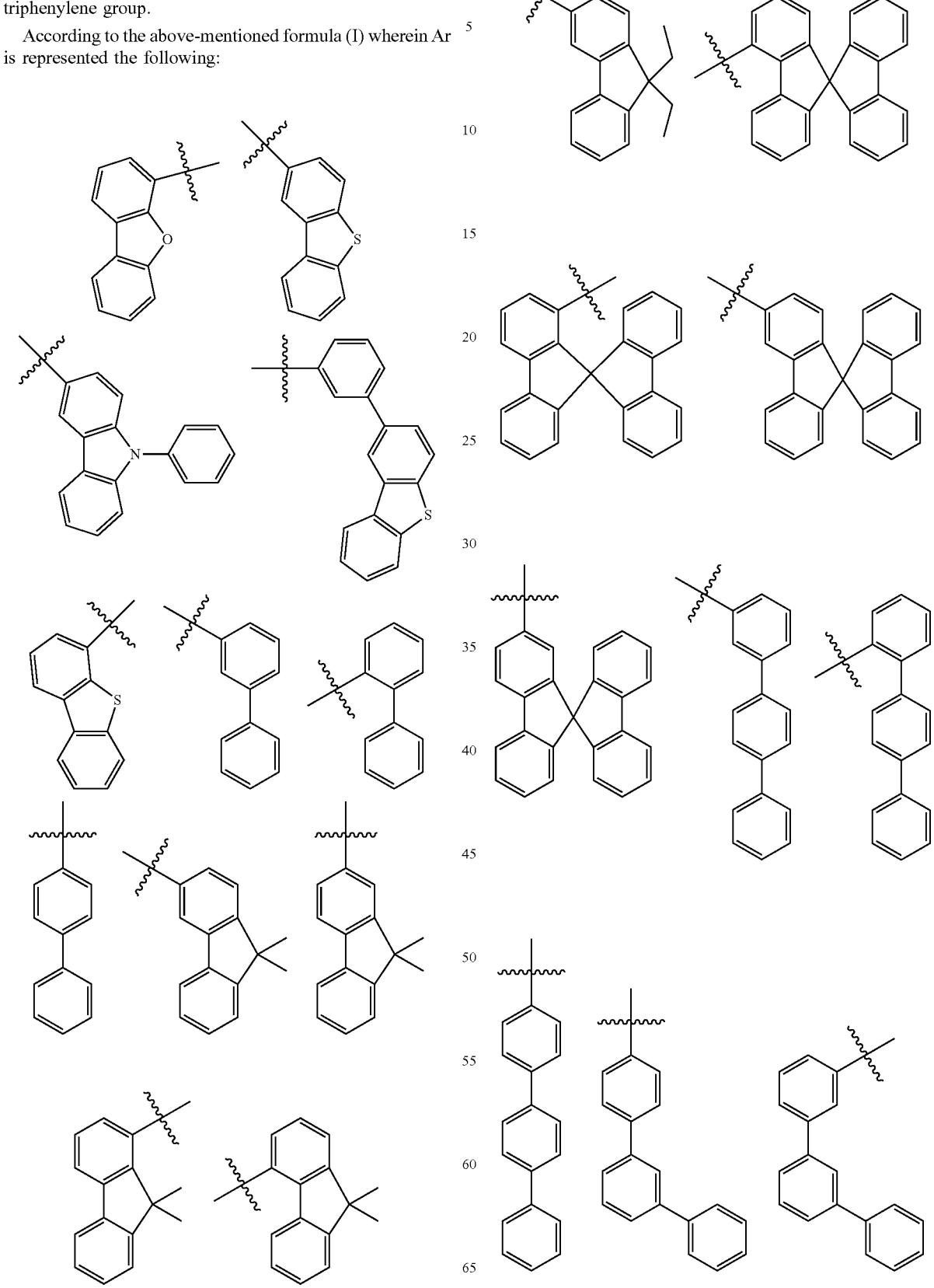

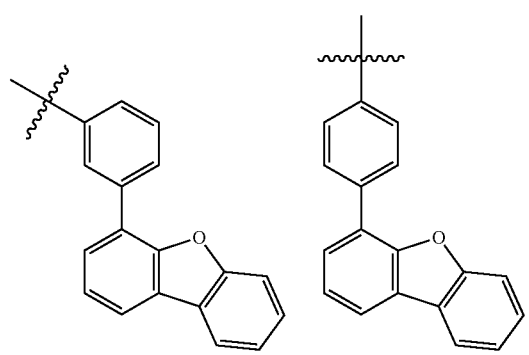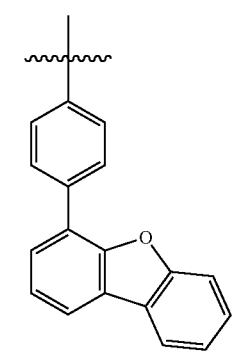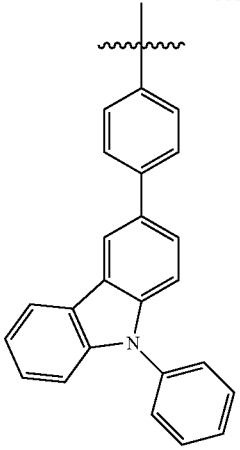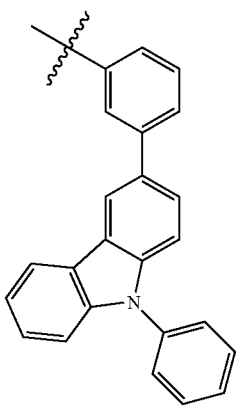
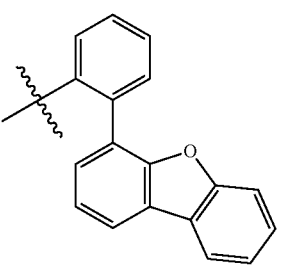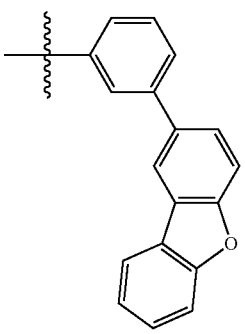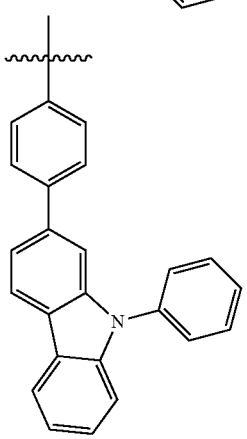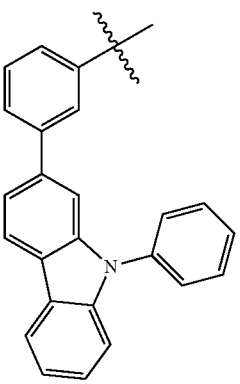
In this embodiment, some specific derivatives are shown below:
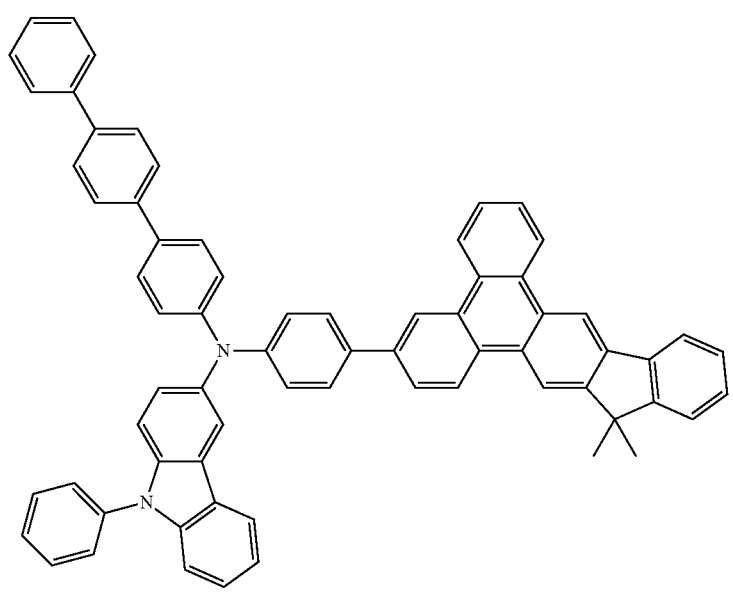
EX1

EX2
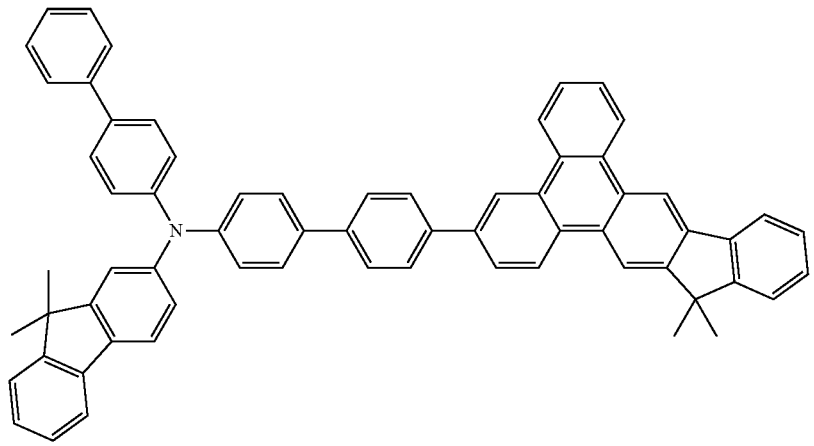
EX3
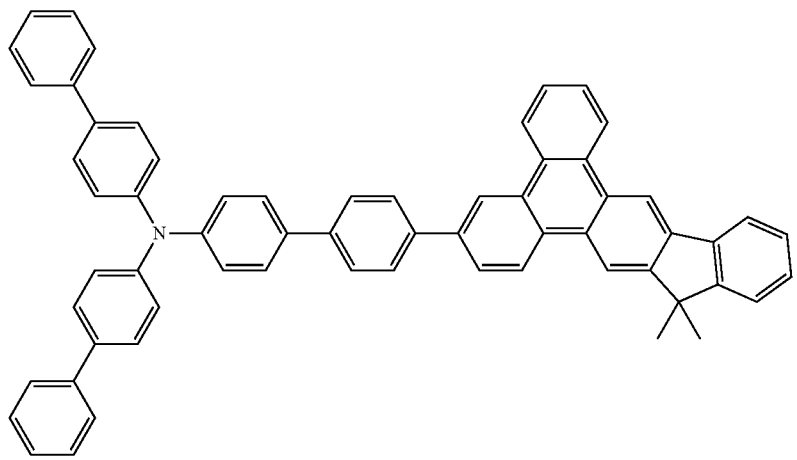
EX4
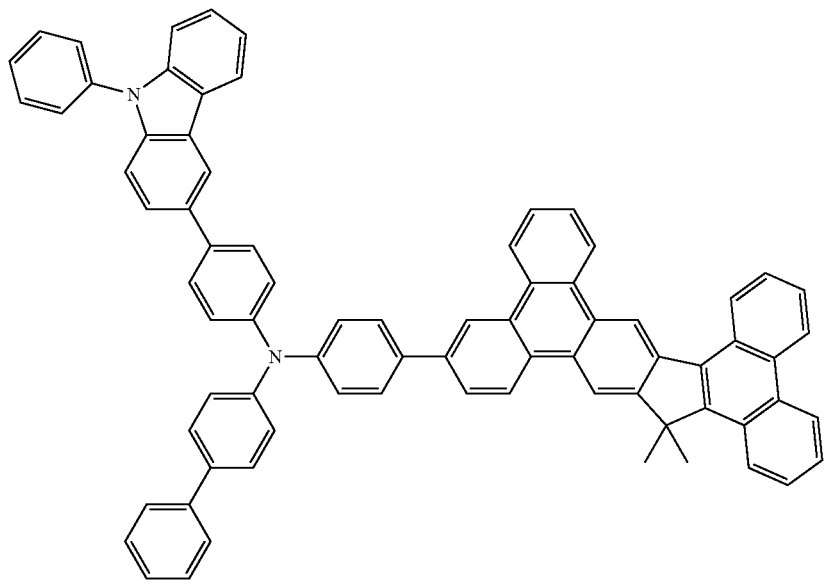

-continued
EX5
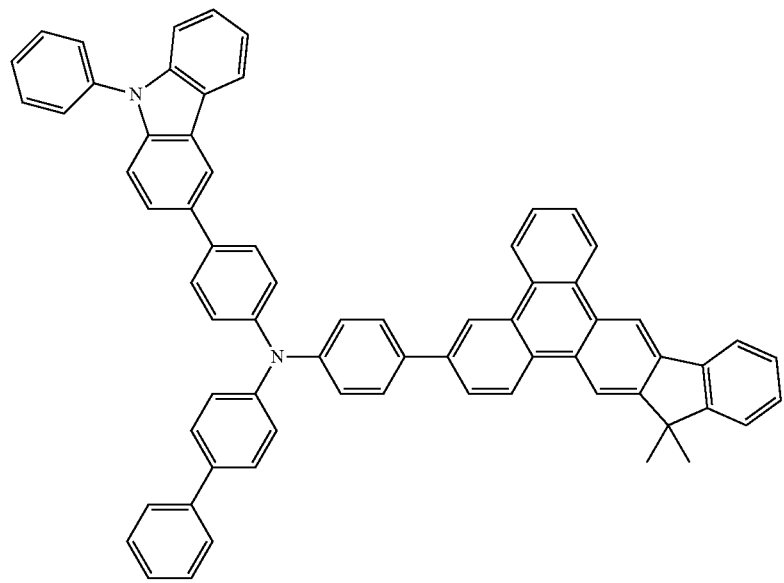
EX6
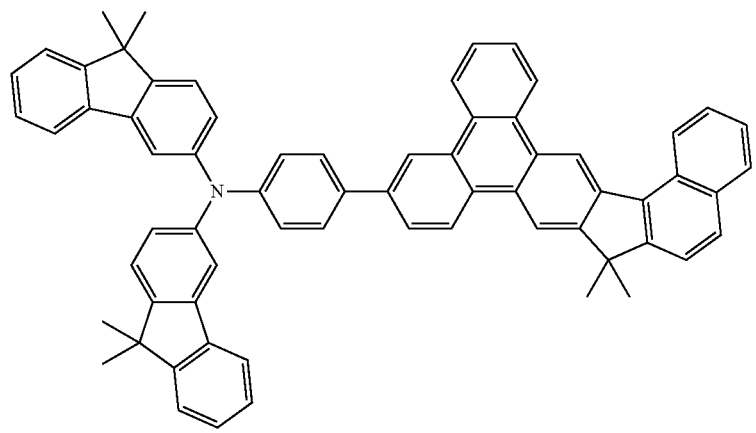
EX7
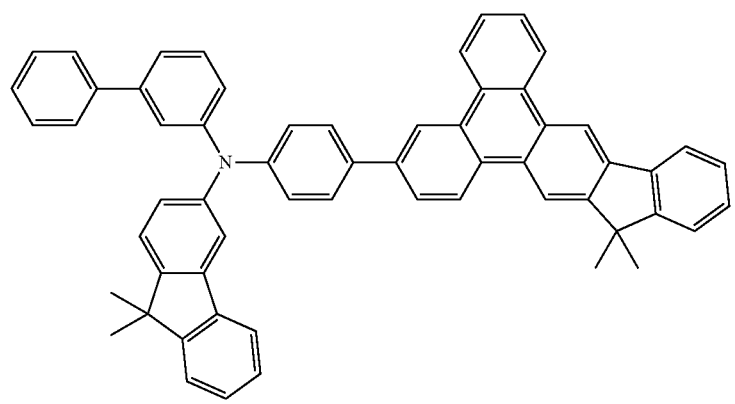

EX8
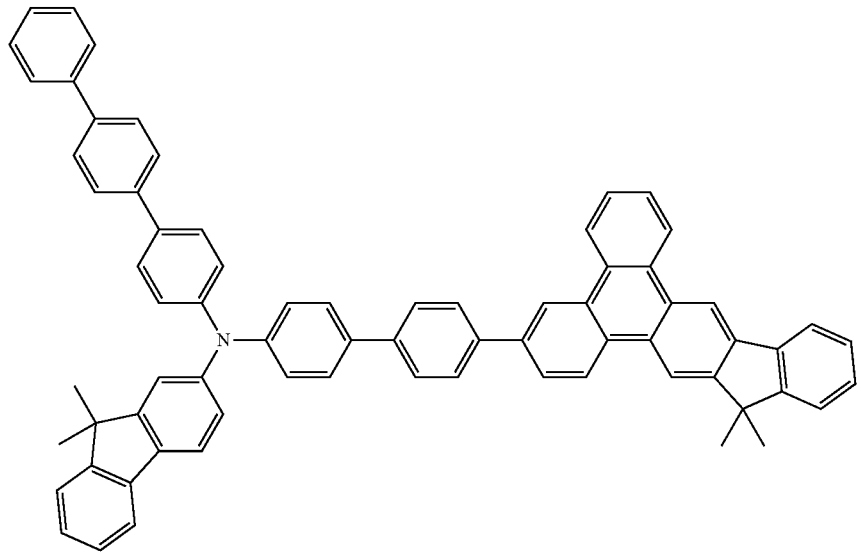
EX9
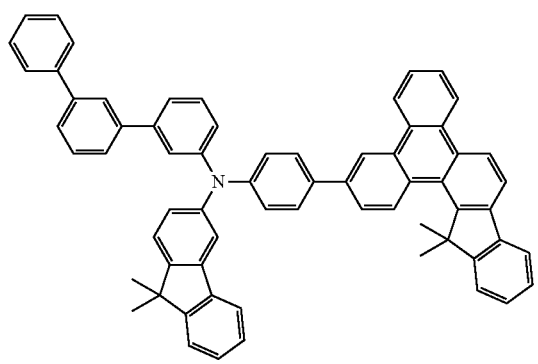
EX10
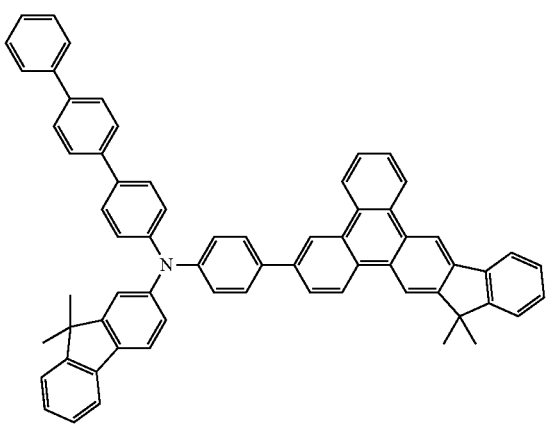
EX11
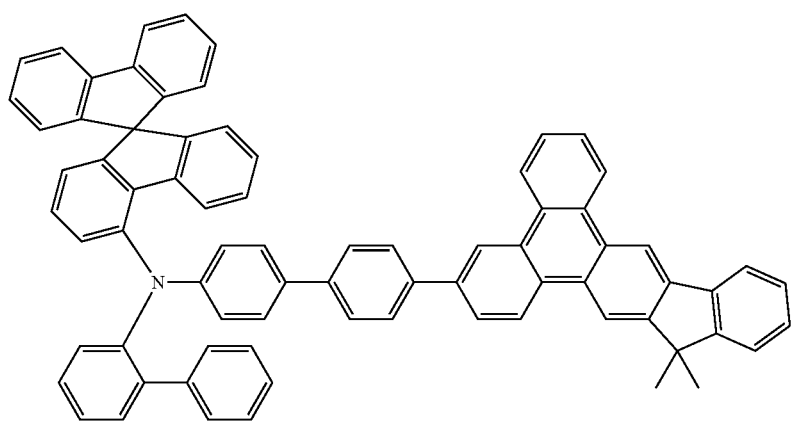

EX12
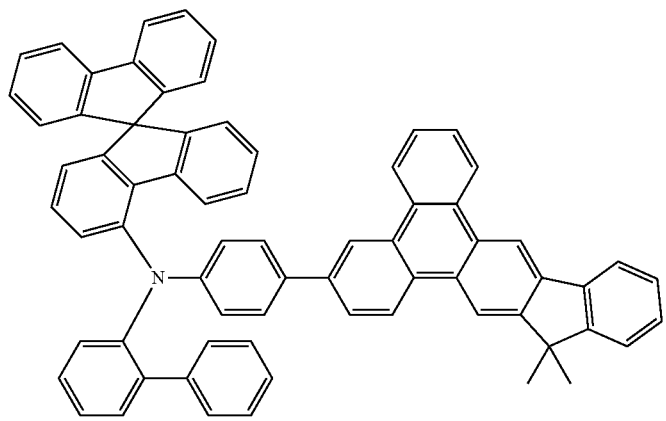
EX13
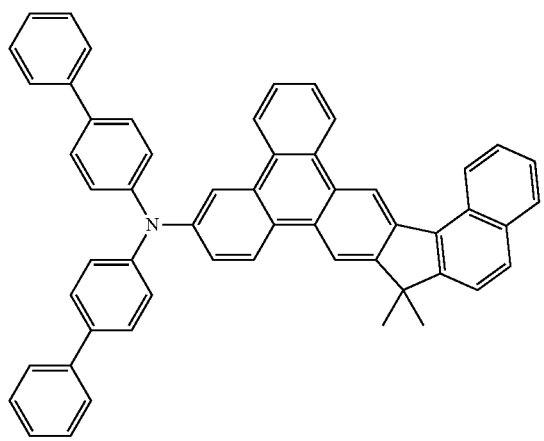
EX14
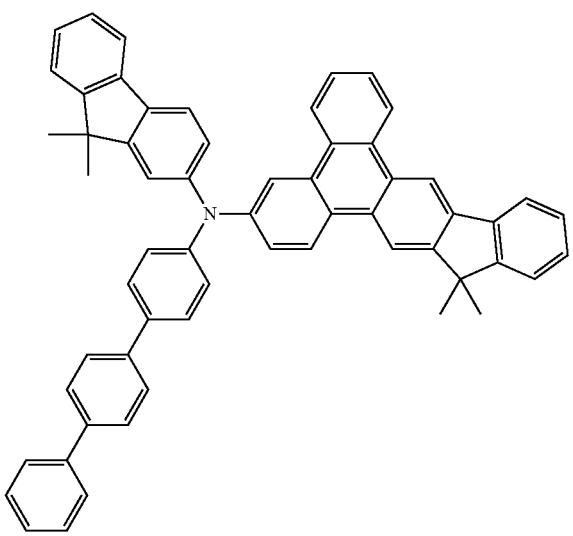
EX15
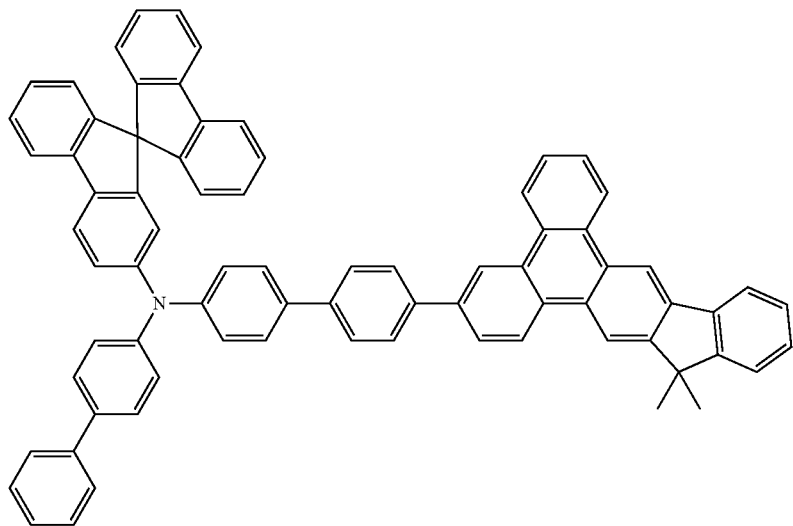

EX16
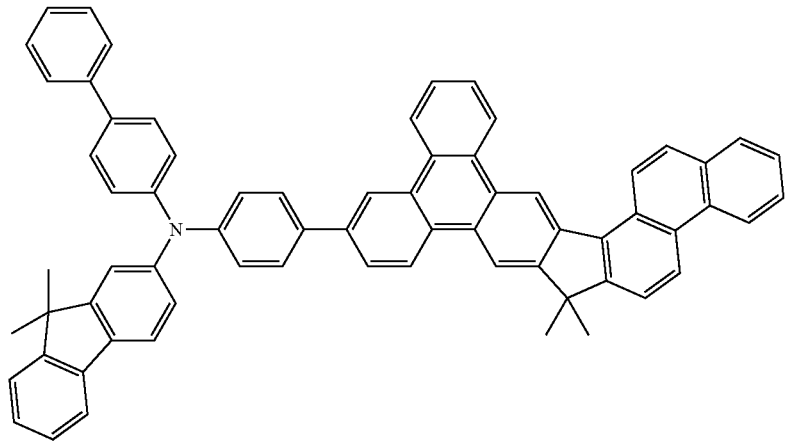
EX17
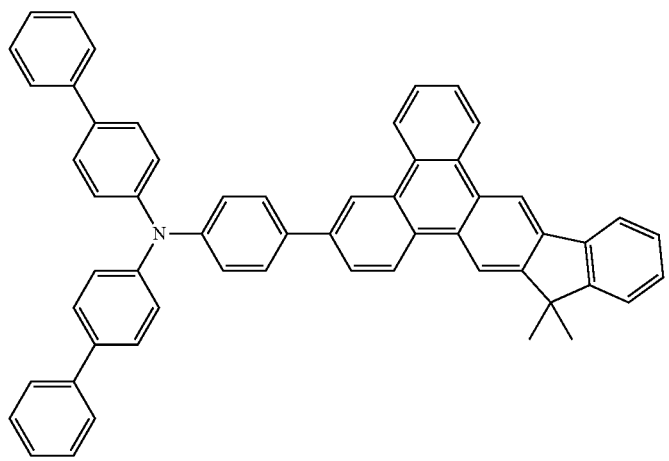
EX18
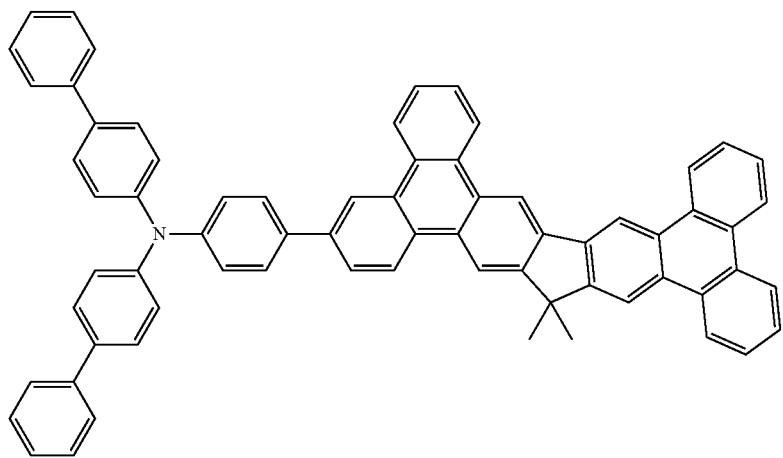

-continued
EX19
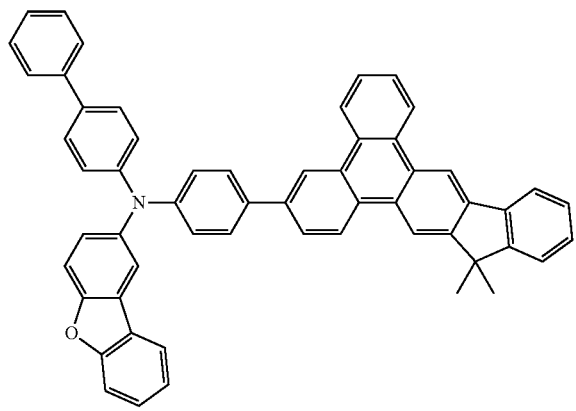
EX20
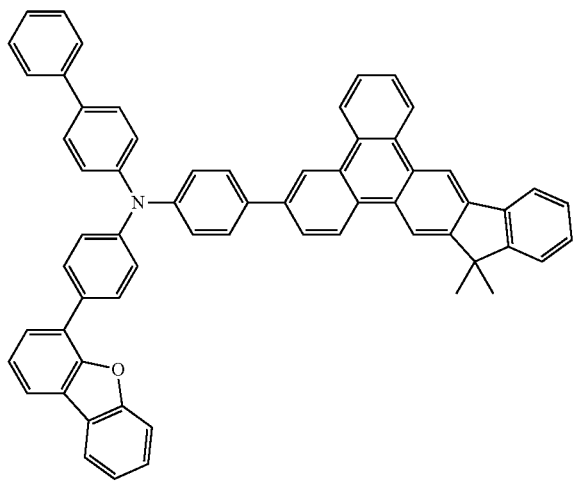
EX21
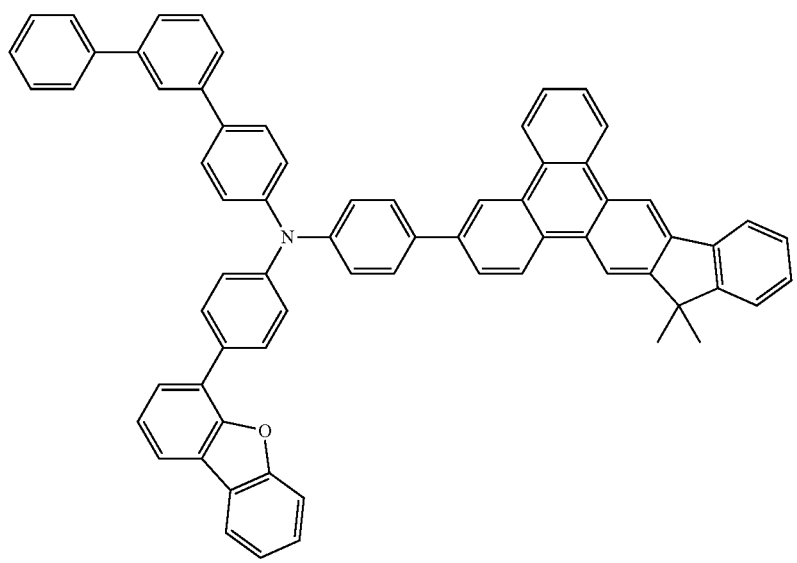
EX22
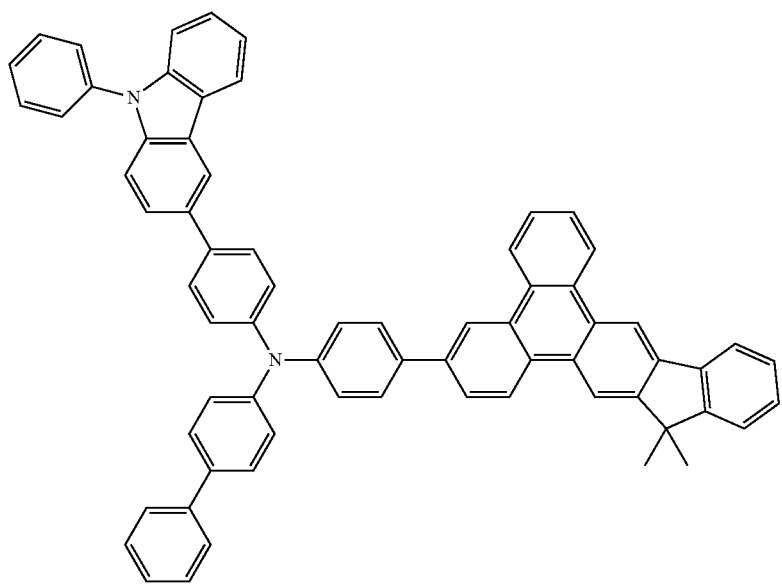

-continued
EX23
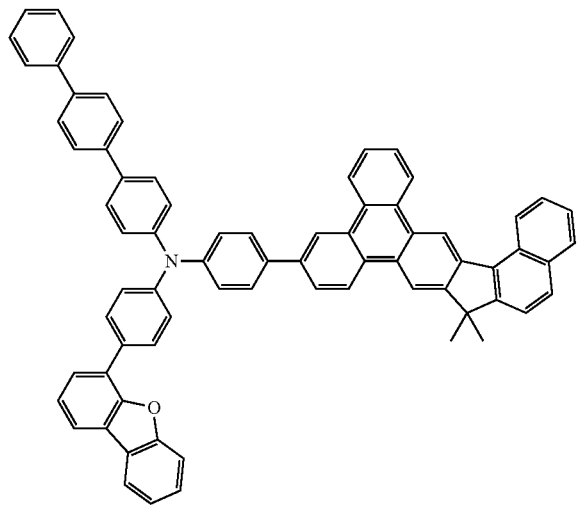
EX24
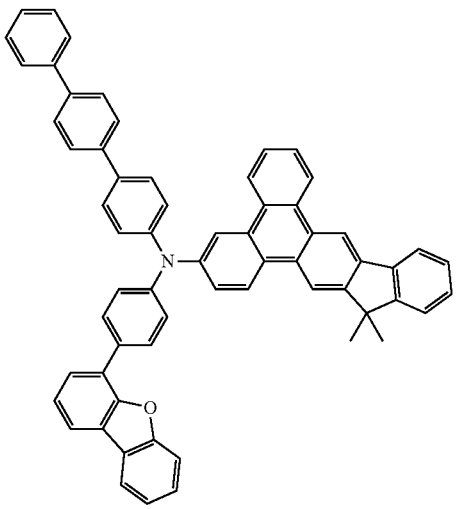
EX25
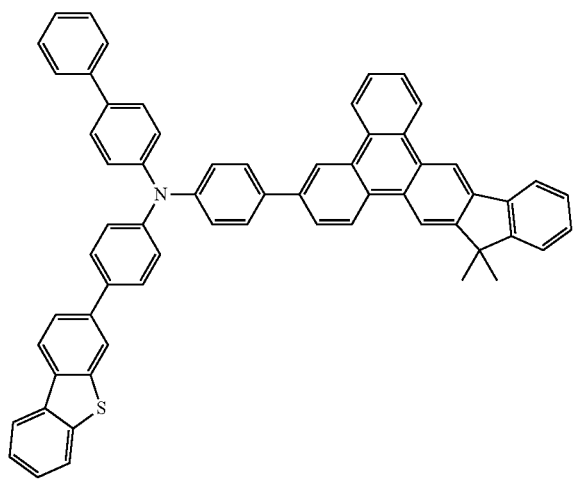
EX26
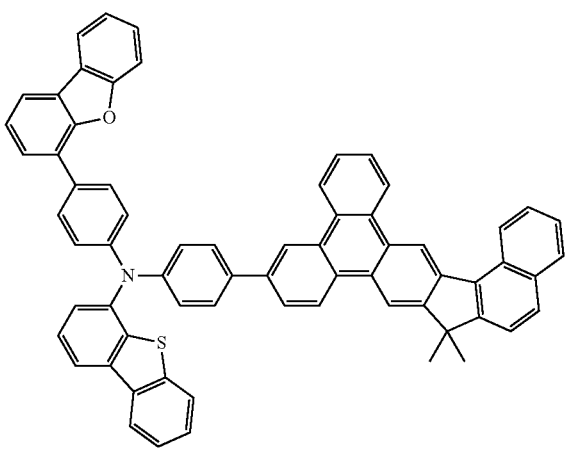
EX27
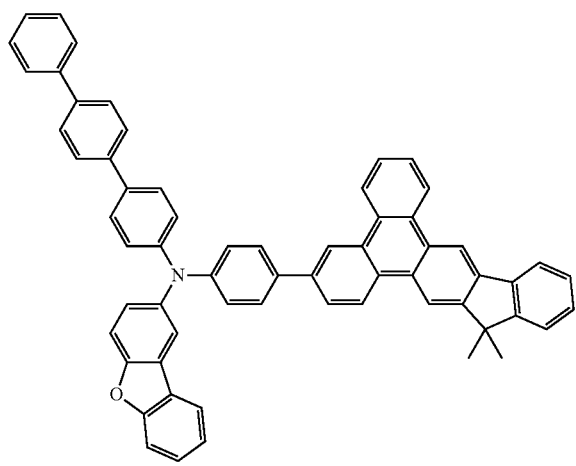
EX28
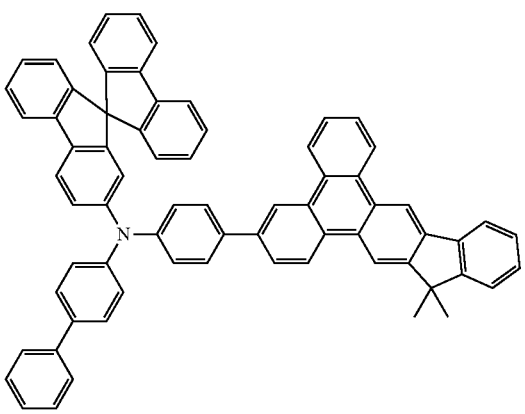

EX29
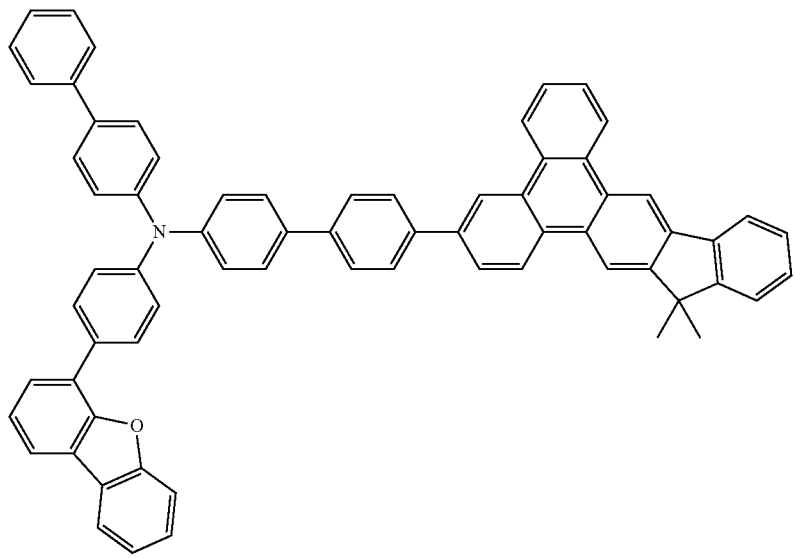
EX30
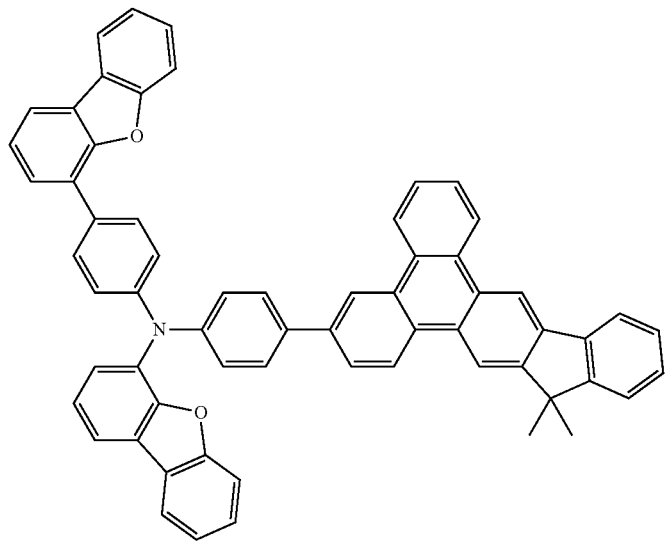

EX31
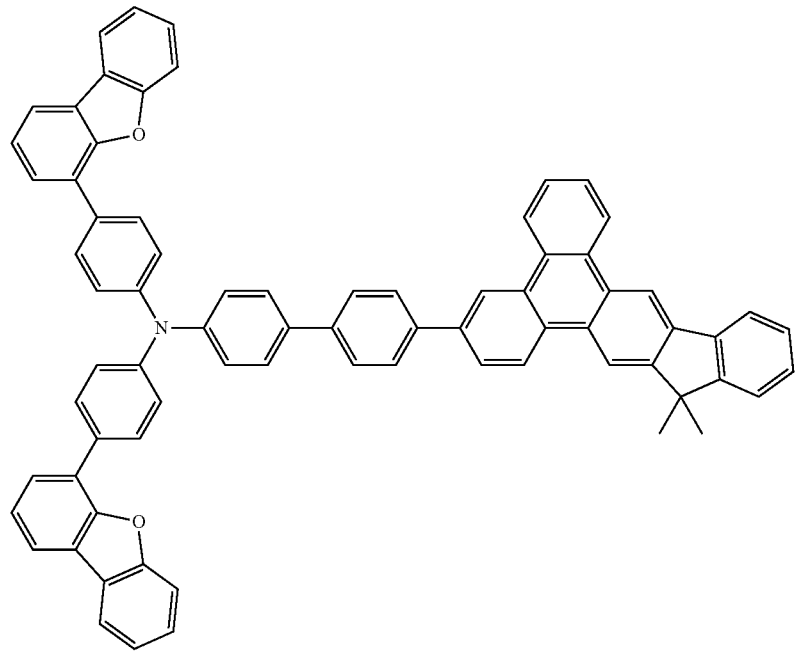
EX32
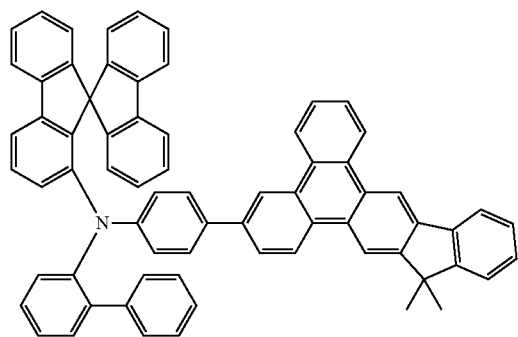
EX33
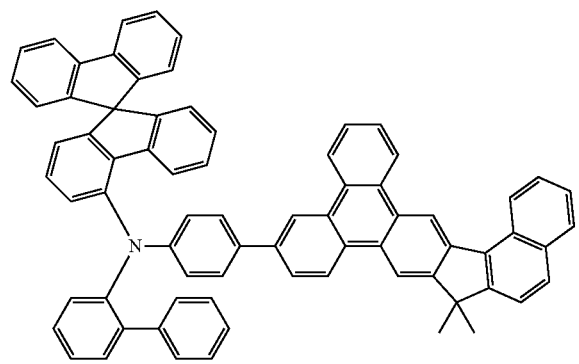
EX34
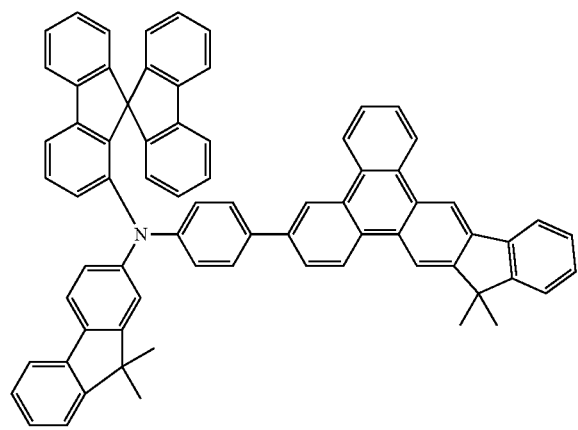
EX35
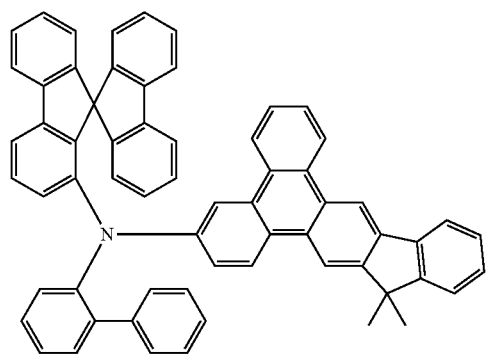

EX36

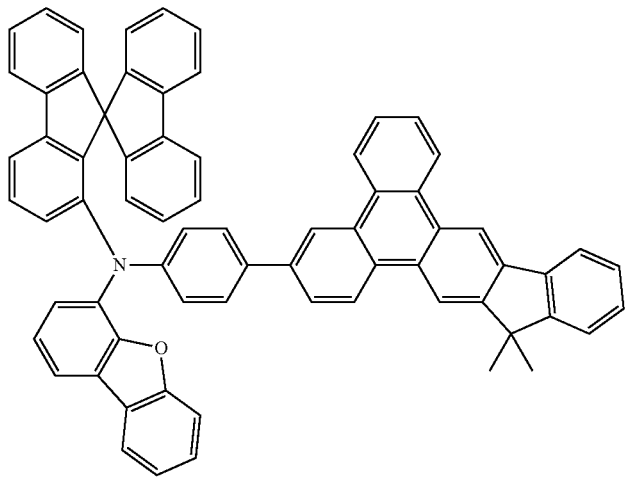

Detailed preparation for the indenotriphenylene-based amine derivative in the present invention could be clarified by exemplary embodiments, but the present invention is not limited to exemplary embodiments. EXAMPLE 1~10 show the preparation for some EXAMPLES of the derivative in the present invention. EXAMPLE 11~12 show the fabrication of organic EL device and I-V-B, half-life time of organic EL device testing report.

Example 1

Synthesis of EX2

Synthesis of 2-bromo-5-nitrobiphenyl

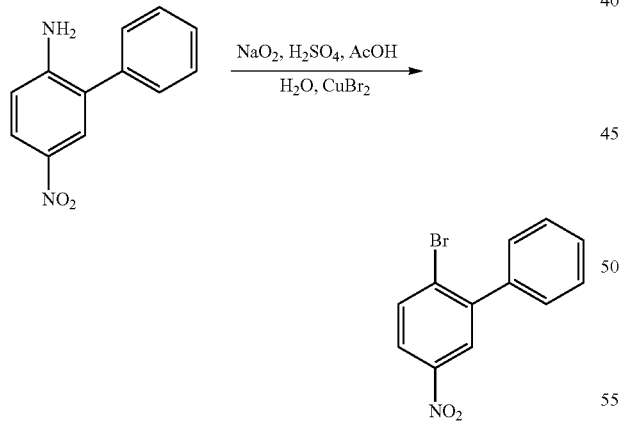

2.6 g (12.14 mmol) of 2-phenyl-4-nitroaniline was added to a mixture of 0.92 g (13.35 mmol) of sodium nitrite, 8 ml of sulfuric acid, 9 ml of acetic acid at 0-5° C. and stirred for 2 hr at 0-5° C. Water was added to this mixture and stirred for 1 hr at room temperature. 4.3 g (19.42 mmol) of copper(II) bromide dissolved in 9.3 ml 2M HCl solution was added and stirred for 20 min at room temperature, then heated to 60° C. for 1 hr. After finishing the reaction, the organic layer was extracted with ether and water, washed with brine, dried over magnesium sulfate and evaporated to dryness and the crude was purified by column chromatography on silica to give product (1.5 g, 5.39 mmol, 45.5%) as a white solid.

Synthesis of
9,9-dimethyl-2-(5-nitrobiphenyl-2-yl)-9H-fluorene

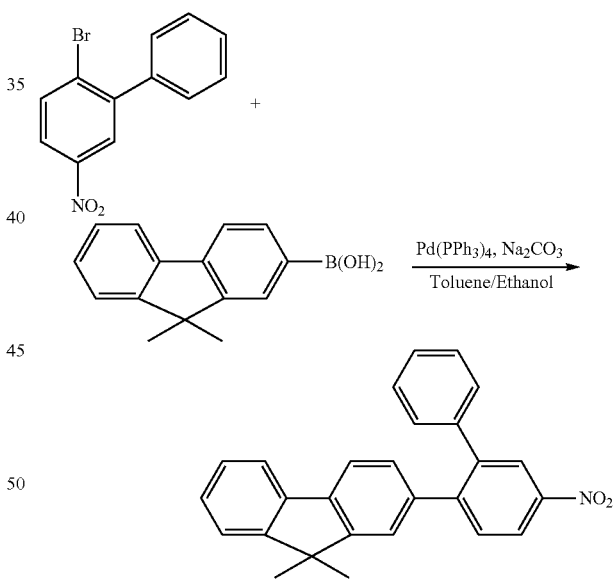

A mixture of 40 g (14.38 mmol) of 2-bromo-5-nitrobiphenyl, 27.7 g (15.82 mmol) of 9,9-dimethyl-9H-fluoren-2-ylboronic acid, 1.8 g (0.16 mmol) of Pd(PPh$_3$)$_4$, 119 ml of 2M Na$_2$CO$_3$, 150 ml of EtOH and 450 ml toluene was degassed and placed under nitrogen, and then heated at 100° C. overnight. After finishing the reaction, the mixture was allowed to cool to room temperature. The solution was extracted with dichloromethane and water. The organic layer was dried with anhydrous magnesium sulfate and the solvent was evaporated under reduced pressure. The residue was purified by column chromatography on silica to give product 43.1 g (110.1 mmol, 69.6%). 1H NMR (CDCl3, 400 MHz):

chemical shift (ppm) 7.93 (s, 1H), 7.71 (d, 1H), 7.50 (d, 1H), 7.38~7.21 (m, 6H), 7.16~6.92 (m, 4H), 6.83~6.65 (m, 2H), 1.15 (s, 6H)

Synthesis of 6-(9,9-dimethyl-9H-fluoren-2-yl)biphenyl-3-amine

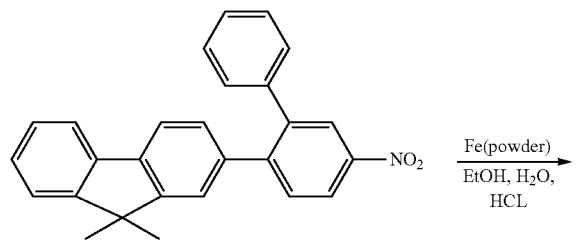

A mixture of 10.4 g (26.56 mmol) of 9,9-dimethyl-2-(5-nitrobiphenyl-2-yl)-9H-fluorene, 8.5 g (159.36 mmol) of iron powder and 10 ml of conc. HCl was refluxed in aqueous ethanol (100 mL of alcohol and 30 mL of water) at 85° C. for 2 h. The reaction mixture was filtered and the filtrate was extracted with ethyl acetate and water. The organic layer was dried with anhydrous magnesium sulfate and the solvent was evaporated under reduced pressure. Formed solid was washed with hexane to yield product 8.2 g (22.68 mmol, 85%). 1H NMR (CDCl3, 400 MHz): chemical shift (ppm) 7.71 (d, 1H), 7.64 (d, 1H), 7.42 (d, 1H), 7.29~7.12 (m, 7H), 7.06 (d, 2H), 6.89 (s, 1H), 6.80 (d, 1H), 6.78 (s, 1H), 4.47 (s, 2H), 1.12 (s, 6H).

Synthesis of 2-(5-bromobiphenyl-2-yl)-9,9-dimethyl-9H-fluorene

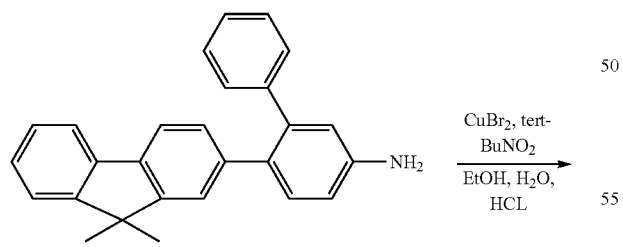

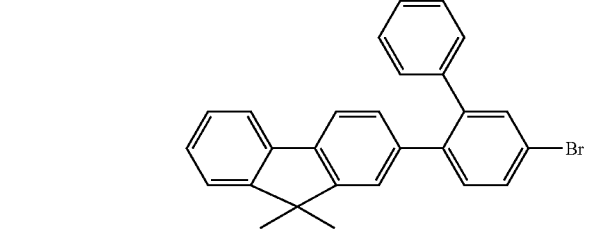

To a refluxing mixture of 0.34 g (3.32 mmol) of tert-butyl nitrite, 0.6 g (2.76 mmol) of anhydrous copper(II) bromide and anhydrous acetonitrile (46 mL), 1 g (2.76 mmol) of the corresponding 6-(9,9-dimethyl-9H-fluoren-2-yl)-biphenyl-3-amine was added slowly over a period of 1 h giving rise to a reaction with vigorous foaming and evolution of nitrogen gas. After completion of the reaction, the mixture was cooled to room temperature and poured into an aqueous HCl solution. The crude which precipitated was purified by column chromatography on silica to give product 0.3 g (0.70 mmol, 25%). 1H NMR (CDCl3, 400 MHz): chemical shift (ppm) 7.81 (d, 1H), 7.68~7.66 (m, 1H), 7.63~7.61 (m, 1H), 7.37~7.35 (m, 1H), 7.32~7.24 (m, 4H), 7.22~7.16 (m, 4H), 7.12~7.09 (m, 2H), 6.93 (d, 1H), 1.20 (s, 6H).

Synthesis of 6-bromo-10,10-dimethyl-10H-indeno[2,1-b]triphenylene

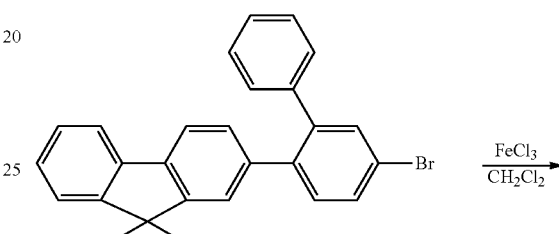

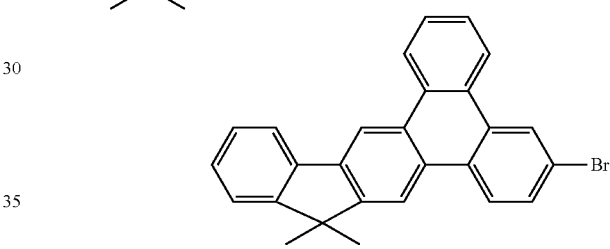

In a 100 ml three-necked flask that had been degassed and filled with nitrogen, 2.9 g (0.68 mmol) of 2-(5-bromobiphenyl-2-yl)-9,9-dimethyl-9H-fluorene was dissolved in anhydrous dichloromethane (180 ml), 5.5 g (3.40 mmol) of iron(III) chloride was then added, and the mixture was stirred one hour. The reaction was quenched with methanol and water and the organic layer was separated and the solvent was removed. The residue was purified by column chromatography on silica afforded a white solid (1.7 g, 0.81 mmol, 58.6%). 1H NMR (CDCl3, 400 MHz): chemical shift (ppm) 9.01 (s, 1H), 8.94 (d, 2H), 8.78 (s, 1H), 8.58 (s, 1H), 8.49 (s, 1H), 7.98 (d, 1H), 7.85~7.78 (m, 2H), 7.63~7.43 (m, 4H), 1.69 (s, 6H).

Synthesis of 2-(10,10-dimethyl-10H-indeno[2,1-b]triphenylen-6-yl)-4,4,5,5-tetramethyl-1,3,2-dioxaborolane

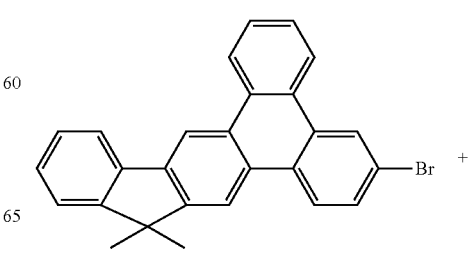 +

-continued

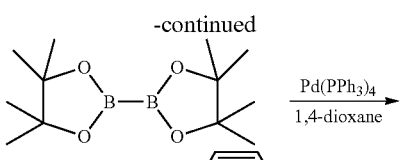

A mixture of 3 g (7 mmol) of 6-bromo-10,10-dimethyl-10H-indeno[2,1-b]triphenylene, 2.16 g (8.4 mmol) of 4,4,4',4',5,5,5',5'-octamethyl-2,2'-bi(1,3,2-dioxaborolane), 0.16 g (0.14 mmol) of Pd(PPh₃)₄, 50 ml 1,4-dioxane was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (2.27 g, 4.8 mmol, 69%) as a white solid.

Synthesis of N-(biphenyl-4-yl)-9,9-dimethyl-9H-fluoren-2-amine

A mixture of 10 g (36.6 mmol) of 2-bromo-9,9-dimethyl-9H-fluorene, 6.2 g (36.6 mmol) of biphenyl-4-amine, 0.08 g (0.37 mmol) of Pd(OAc)₂, 7.04 g (73.2 mmol) of sodium tert-butoxide, and 200 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (5.7 g, 15.7 mmol, 43%) as a yellow solid.

Synthesis of N-(biphenyl-4-yl)-N-(4'-bromobiphenyl-4-yl)-9,9-dimethyl-9H-fluoren-2-amine

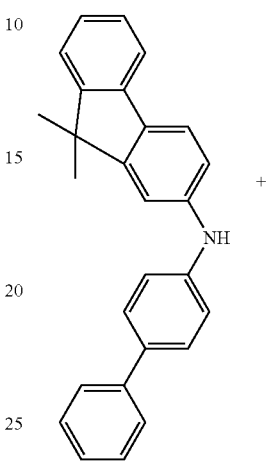

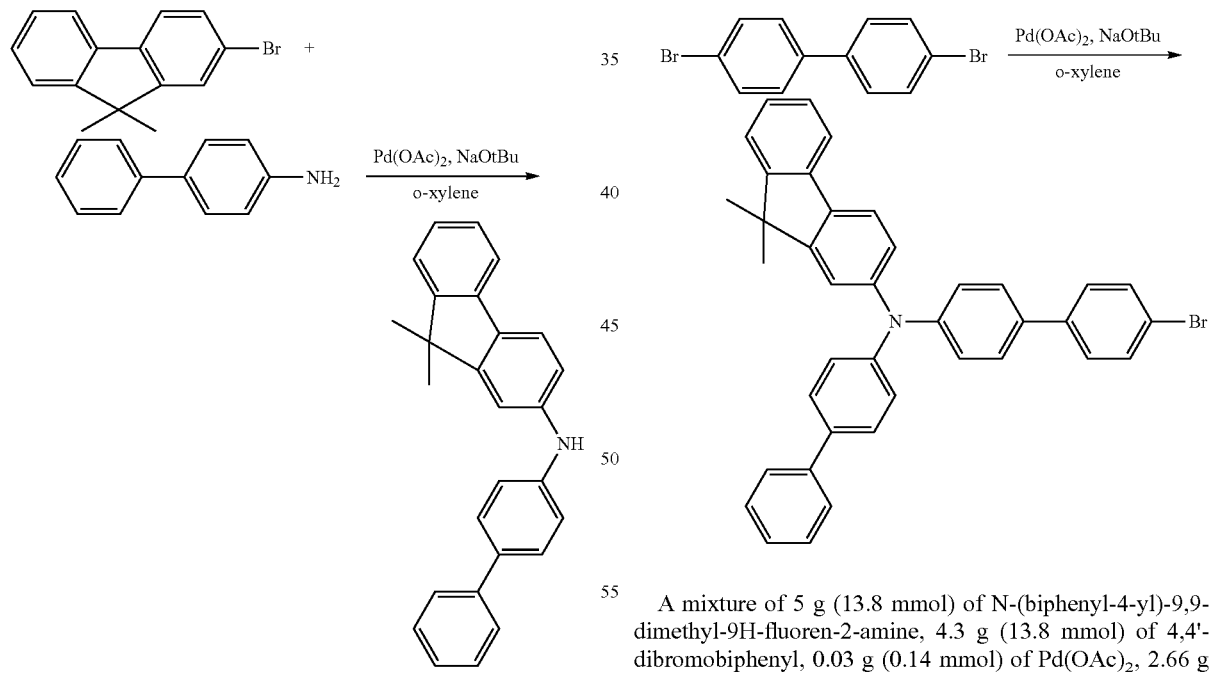

A mixture of 5 g (13.8 mmol) of N-(biphenyl-4-yl)-9,9-dimethyl-9H-fluoren-2-amine, 4.3 g (13.8 mmol) of 4,4'-dibromobiphenyl, 0.03 g (0.14 mmol) of Pd(OAc)₂, 2.66 g (27.6 mmol) of sodium tert-butoxide, and 100 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (3.2 g, 5.4 mmol, 39%) as a yellow solid.

Synthesis of N-(biphenyl-4-yl)-N-(4'-(10,10-dimethyl-10H-indeno[2,1-b]triphenylen-6-yl)biphenyl-4-yl)-9,9-dimethyl-9H-fluoren-2-amine

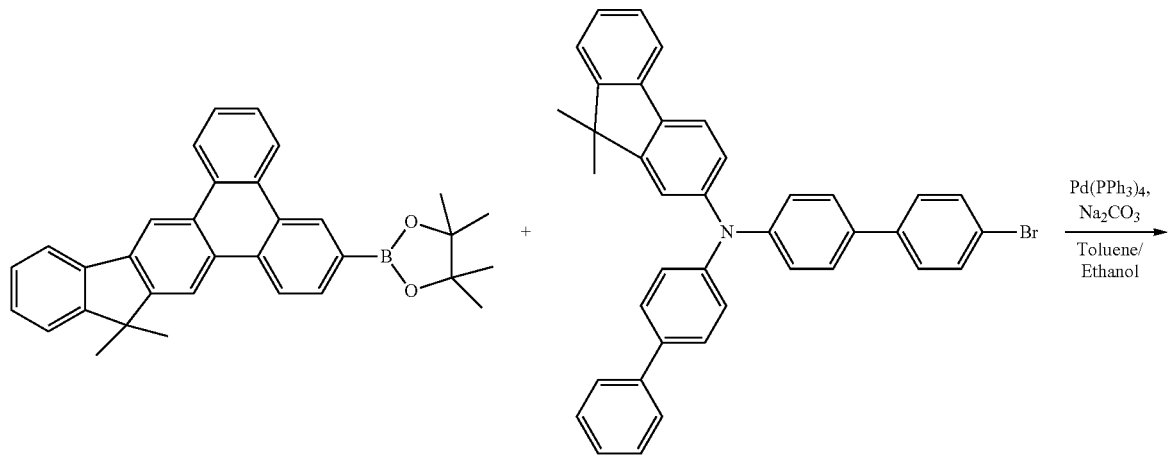

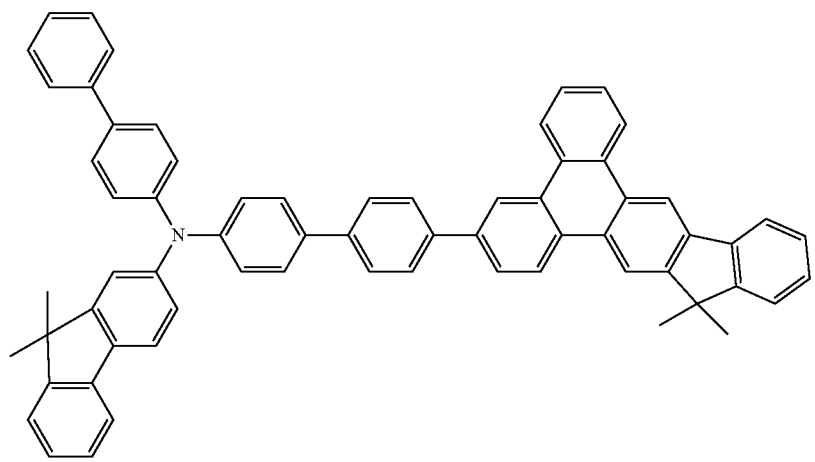

A mixture of 2 g (4.25 mmol) of 2-(10,10-dimethyl-10H-indeno[2,1-b]triphenylen-6-yl)-4,4,5,5-tetramethyl-1,3,2-dioxaborolane, 2.77 g (4.68 mmol) of N-(biphenyl-4-yl)-N-(4'-bromobiphenyl-4-yl)-9,9-dimethyl-9H-fluoren-2-amine, 0.05 g (0.04 mmol) of Pd(PPh$_3$)$_4$, 4.25 ml of 2M Na$_2$CO$_3$, 10 ml of EtOH and 30 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (2.37 g, 2.77 mmol, 65%) as a white solid. 1H NMR (CDCl3, 400 MHz): chemical shift (ppm) 9.07~8.93 (m, 3H), 8.34~8.17 (m, 5H), 7.98~7.79 (m, 8H), 7.68~7.53 (m, 8H), 7.44~7.28 (m, 7H), 7.01~6.85 (m, 6H), 1.79 (s, 6H), 1.73 (s, 6H). MS (m/z, FAB$^+$): 856.7.

Example 2

Synthesis of EX3

Synthesis of N,N-di(biphenyl-4-yl)-4'-(10,10-dimethyl-10H-indeno[2,1-b]triphenylen-6-yl)biphenyl-4-amine

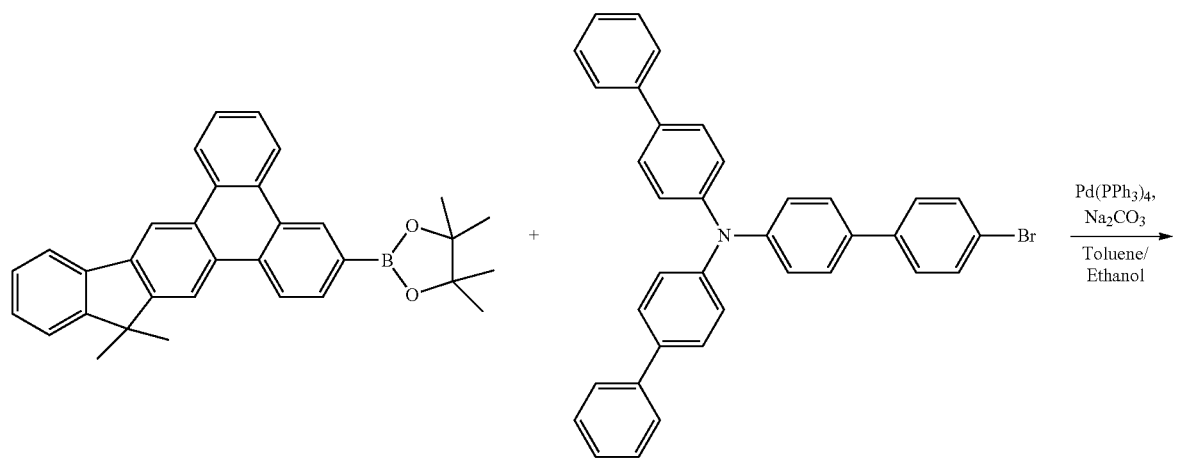

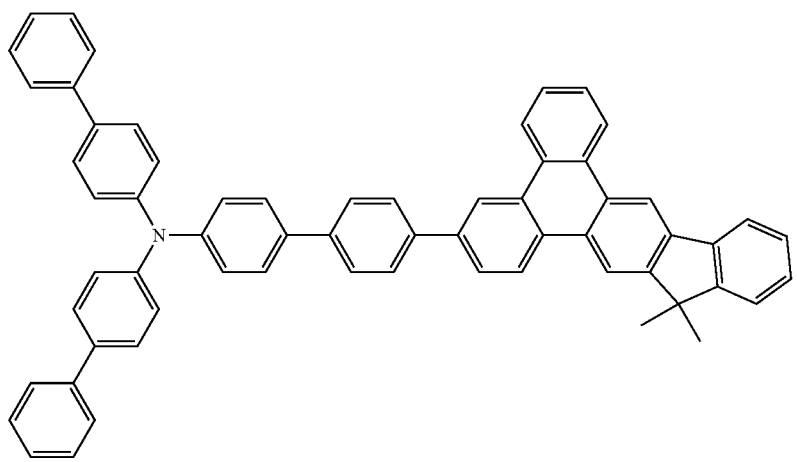

N-(biphenyl-4-yl)-N-(4'-bromobiphenyl-4-yl)biphenyl-4-amine instead of N-(biphenyl-4-yl)-N-(4'-bromobiphenyl-4-yl)-9,9-dimethyl-9H-fluoren-2-amine, except for using the same method as in synthesis example 1, the desired compound of N,N-di(biphenyl-4-yl)-4'-(10,10-dimethyl-10H-indeno[2,1-b]triphenylen-6-yl)biphenyl-4-amine (2.36 g, yield=68%) was obtained. MS (m/z, FAB$^+$): 816.8

Example 3

Synthesis of EX8

Synthesis of N-(triphenyl-4-yl)-N-(4'-(10,10-dimethyl-10H-indeno[2,1-b]triphenylen-6-yl)biphenyl-4-yl)-9,9-dimethyl-9H-fluoren-2-amine

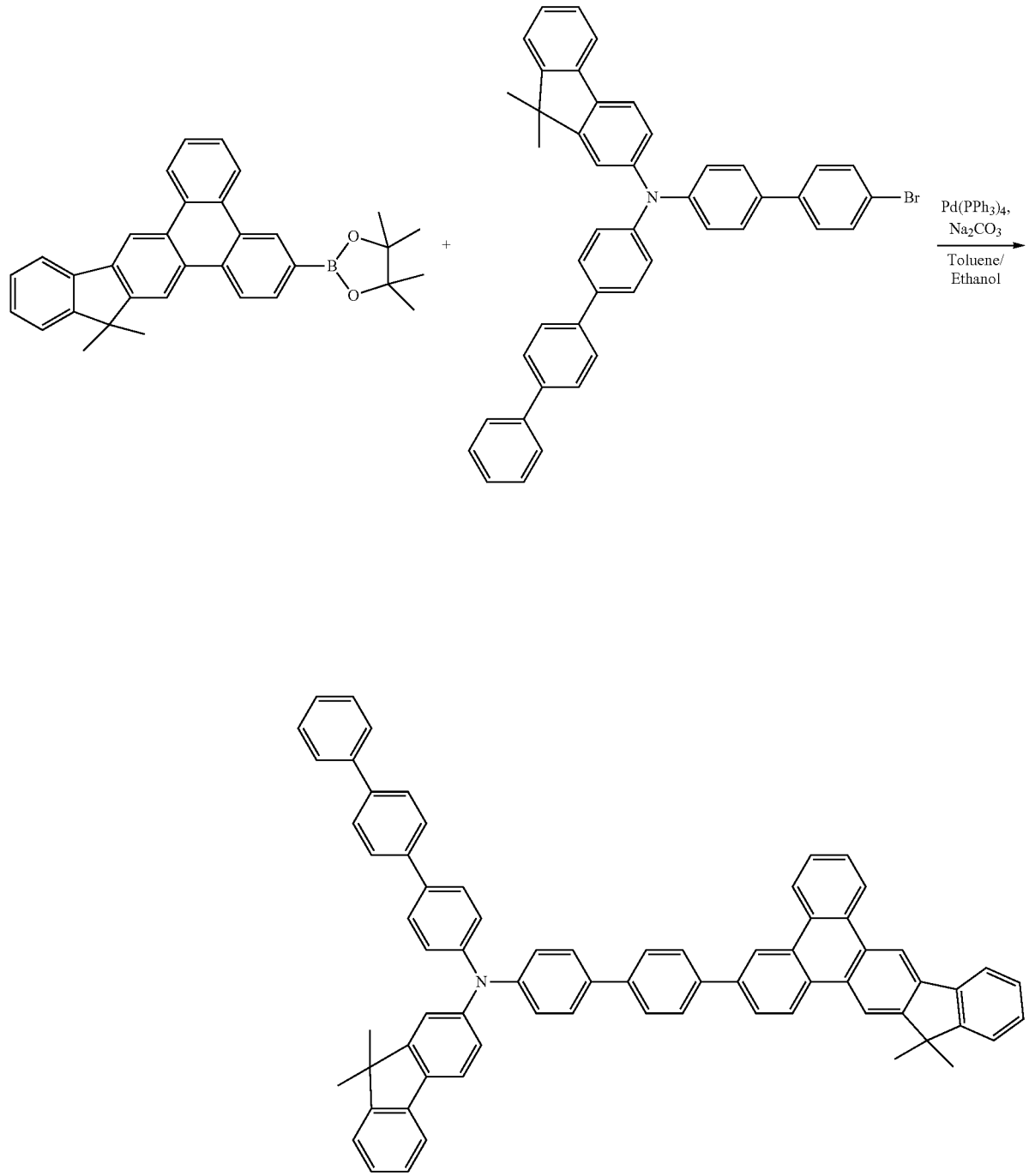

N-(triphenyl-4-yl)-N-(4'-bromobiphenyl-4-yl)-9,9-dimethyl-9H-fluoren-2-amine instead of N-(biphenyl-4-yl)-N-(4'-bromobiphenyl-4-yl)-9,9-dimethyl-9H-fluoren-2-amine, except for using the same method as in synthesis example 1, the desired compound of N-(triphenyl-4-yl)-N-(4'-(10,10-dimethyl-10H-indeno[2,1-b]triphenylen-6-yl)biphenyl-4-yl)-9,9-dimethyl-9H-fluoren-2-amine (2.34 g, yield=59%) was obtained. MS (m/z, FAB$^+$): 931.8

Example 4

Synthesis of EX11

Synthesis of N-(biphenyl-2-yl)-9,9'-spirobi[fluoren]-4-amine

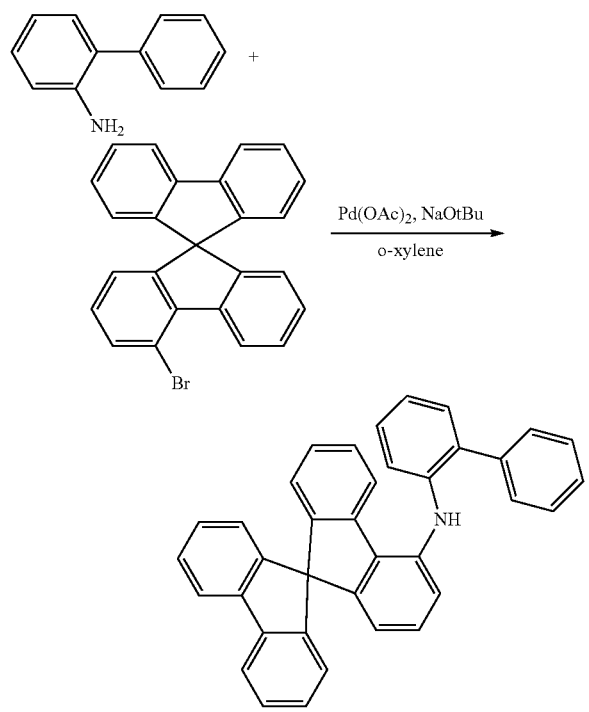

A mixture of 5 g (29.5 mmol) of biphenyl-2-amine, 11.68 g (29.5 mmol) of 4-bromo-9,9'-spirobi[fluorene], 0.066 g (0.3 mmol) of Pd(OAc)$_2$, 5.68 g (59 mmol) of sodium tert-butoxide, and 200 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (5.86 g, 12.1 mmol, 41%) as a yellow solid.

Synthesis of N-(biphenyl-2-yl)-N-(4'-bromobiphenyl-4-yl)-9,9'-spirobi[fluoren]-4-amine

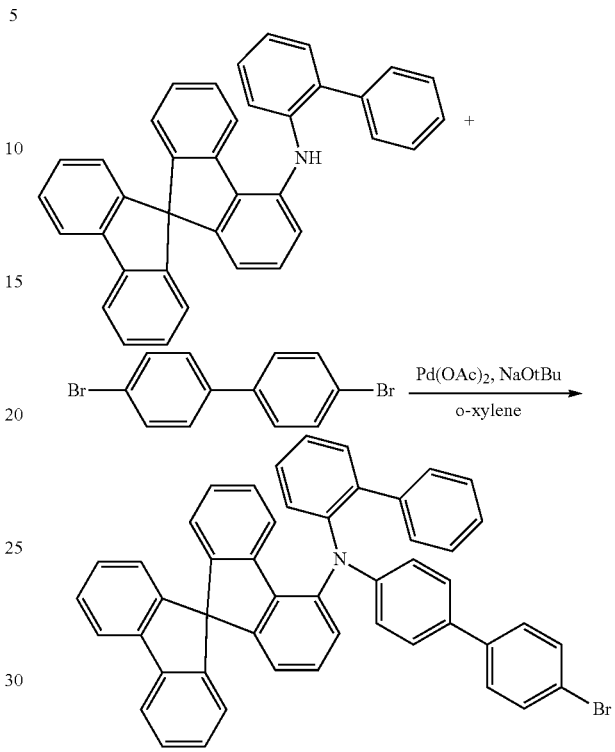

A mixture of 5 g (10.3 mmol) of N-(biphenyl-2-yl)-9,9'-spirobi[fluoren]-4-amine, 3.23 g (10.3 mmol) of 4,4'-dibromobiphenyl, 0.02 g (0.1 mmol) of Pd(OAc)$_2$, 1.99 g (20.6 mmol) of sodium tert-butoxide, and 100 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (2.59 g, 3.62 mmol, 35%) as a yellow solid.

Synthesis of N-(biphenyl-2-yl)-N-(4'-(10,10-dimethyl-10H-indeno[2,1-b]triphenylen-6-yl)biphenyl-4-yl)-9,9'-spirobi[fluoren]-4-amine

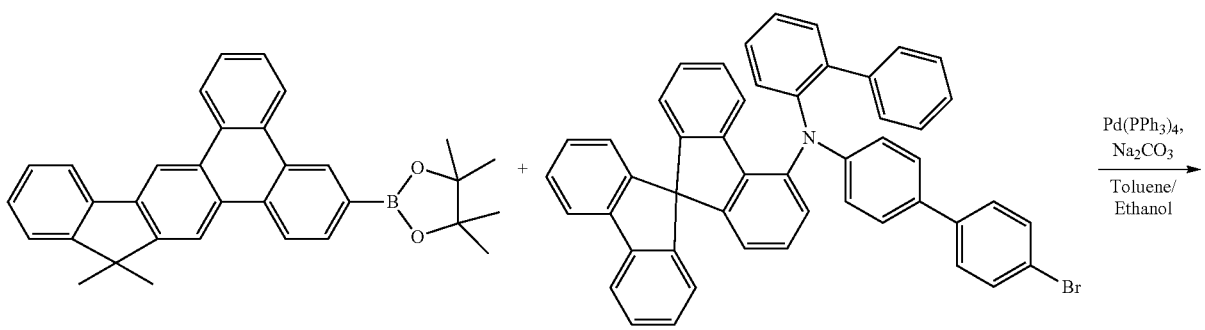

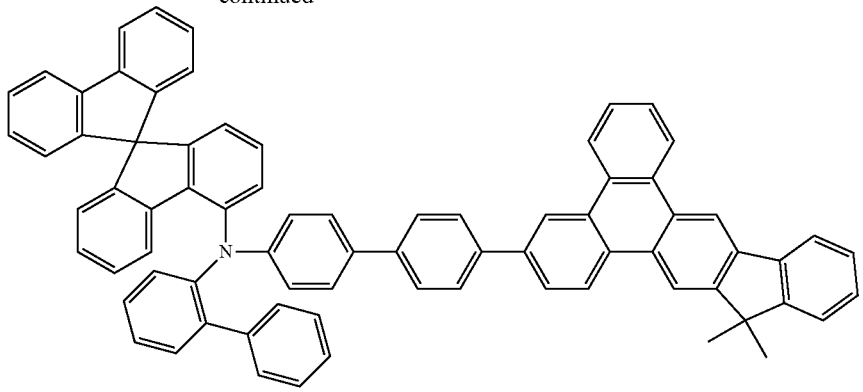

A mixture of 2 g (4.25 mmol) of 2-(10,10-dimethyl-10H-indeno[2,1-b]triphenylen-6-yl)-4,4,5,5-tetramethyl-1,3,2-dioxaborolane, 3.34 g (4.68 mmol) of N-(biphenyl-2-yl)-N-(4'-bromobiphenyl-4-yl)-9,9'-spirobi[fluoren]-4-amine, 0.05 g (0.04 mmol) of Pd(PPh$_3$)$_4$, 4.25 ml of 2M Na$_2$CO$_3$, 10 ml of EtOH and 30 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (1.75 g, 1.78 mmol, 42%) as a white solid. 1H NMR (CDCl3, 400 MHz): chemical shift (ppm) 9.06~8.94 (m, 3H), 8.32~8.15 (m, 5H), 7.91~7.78 (m, 2H), 7.77~7.66 (m, 4H), 7.54~7.39 (m, 8H), 7.28~7.16 (m, 16H), 7.01~6.87 (m, 7H), 1.789 (s, 6H). MS (m/z, FAB$^+$): 978.2

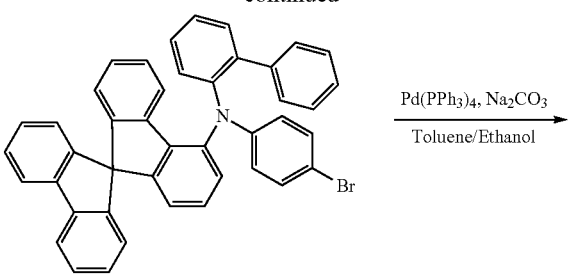

Example 5

Synthesis of EX12

Synthesis of N-(biphenyl-2-yl)-N-(4-(10,10-dimethyl-10H-indeno[2,1-b]triphenylen-6-yl)phenyl)-9,9'-spirobi[fluoren]-4-amine

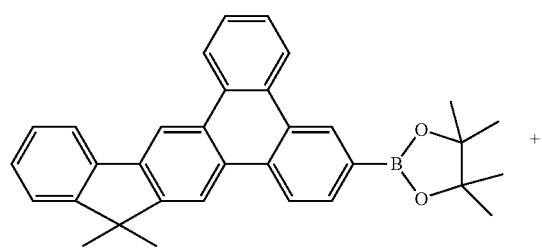

N-(biphenyl-2-yl)-N-(4-bromophenyl)-9,9'-spirobi[fluoren]-4-amine instead of N-(biphenyl-2-yl)-N-(4'-bromobiphenyl-4-yl)-9,9'-spirobi[fluoren]-4-amine, except for using the same method as in synthesis example 4, the desired compound of N-(biphenyl-2-yl)-N-(4-(10,10-dimethyl-10H-indeno[2,1-b]triphenylen-6-yl)phenyl)-9,9'-spirobi[fluoren]-4-amine (1.4 g, yield=37%) was obtained. MS (m/z, FAB$^+$): 902.7

Example 6

Synthesis of EX15

Synthesis of N-(biphenyl-4-yl)-N-(4'-(10,10-dimethyl-10H-indeno[2,1-b]triphenylen-6-yl)biphenyl-4-yl)-9,9'-spirobi[fluoren]-2-amine

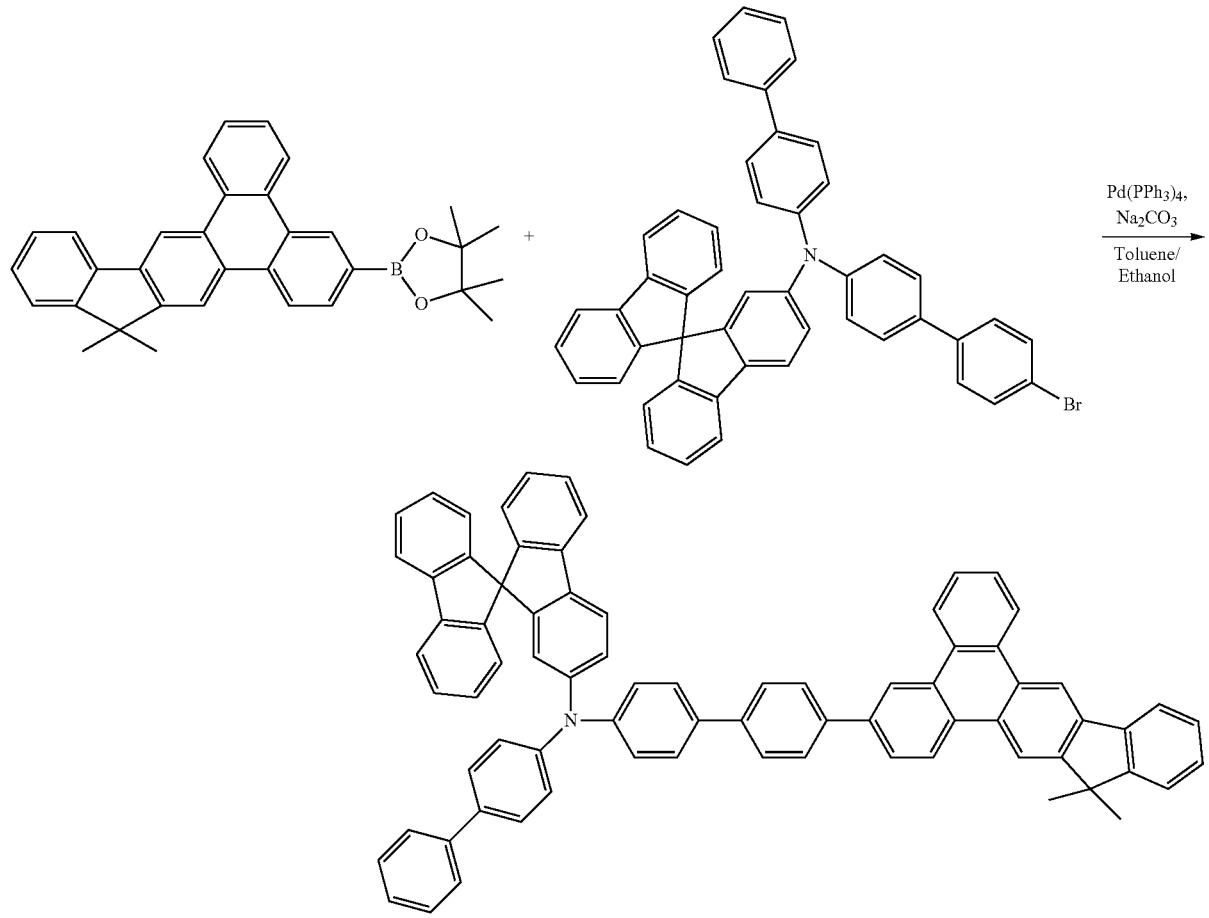

N-(biphenyl-4-yl)-N-(4'-bromobiphenyl-4-yl)-9,9'-spirobi[fluoren]-2-amine instead of N-(biphenyl-2-yl)-N-(4'-bromobiphenyl-4-yl)-9,9'-spirobi[fluoren]-4-amine, except for using the same method as in synthesis example 4, the desired compound of N-(biphenyl-4-yl)-N-(4'-(10,10-dimethyl-10H-indeno[2,1-b]triphenylen-6-yl)biphenyl-4-yl)-9,9'-spirobi[fluoren]-2-amine (1.58 g, yield=38%) was obtained. MS (m/z, FAB$^+$): 978.6

Example 7

Synthesis of EX22

Synthesis of N-(4-(9-phenyl-9H-carbazol-3-yl)phenyl)biphenyl-4-amine

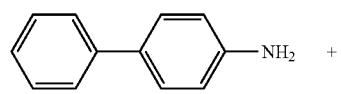

+

-continued

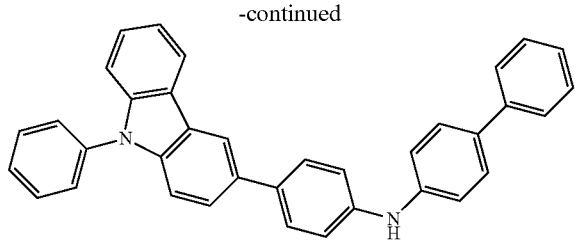

A mixture of 10 g (59.1 mmol) of biphenyl-4-amine, 23.5 g (59.1 mmol) of 3-(4-bromophenyl)-9-phenyl-9H-carbazole, 0.13 g (0.59 mmol) of Pd(OAc)$_2$, 11.36 g (118 mmol) of sodium tert-butoxide, and 400 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (12.36 g, 25.4 mmol, 43%) as a yellow solid.

Synthesis of N-(4-bromophenyl)-N-(4-(9-phenyl-9H-carbazol-3-yl)phenyl)biphenyl-4-amine

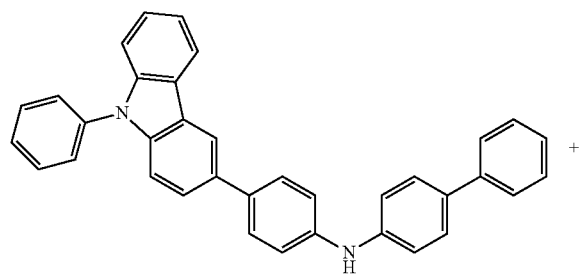

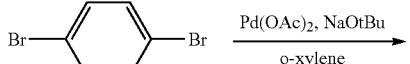

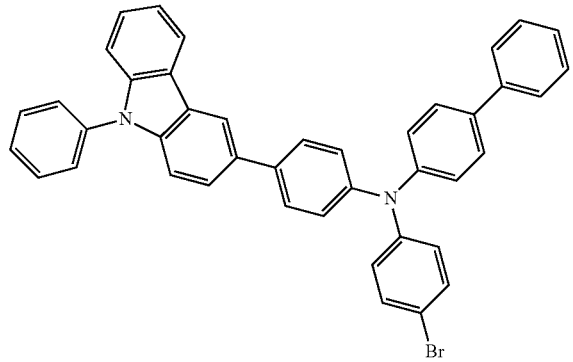

A mixture of 5 g (10.3 mmol) of N-(4-(9-phenyl-9H-carbazol-3-yl)phenyl)biphenyl-4-amine, 2.42 g (10.3 mmol) of 1,4-dibromobenzene, 0.02 g (0.1 mmol) of Pd(OAc)$_2$, 1.97 g (20.5 mmol) of sodium tert-butoxide, and 100 ml of o-xylene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (2.44 g, 3.8 mmol, 37%) as a yellow solid.

Synthesis of N-(4-(10,10-dimethyl-10H-indeno[2,1-b]triphenylen-6-yl)phenyl)-N-(4-(9-phenyl-9H-carbazol-3-yl)phenyl)biphenyl-4-amine

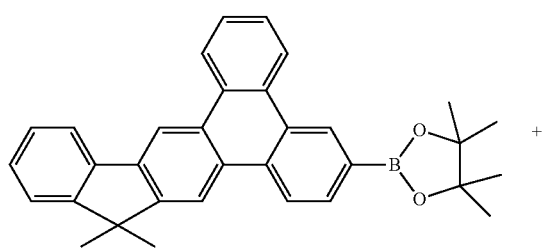

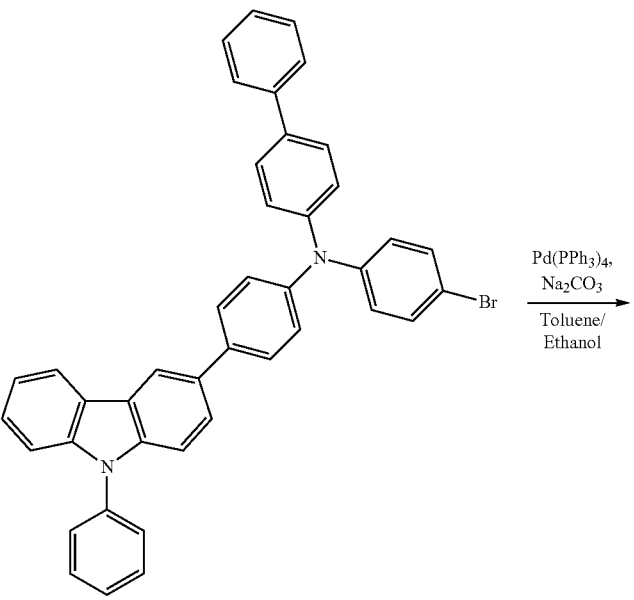

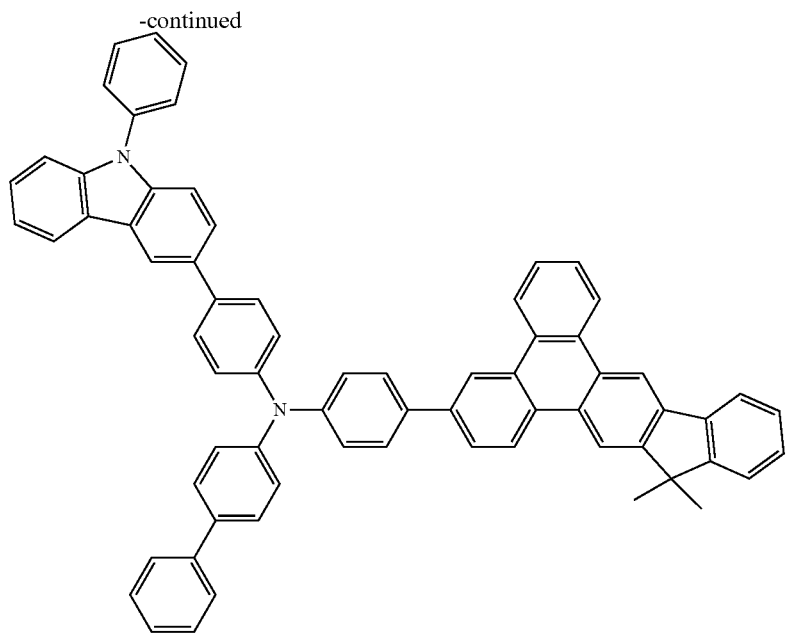

A mixture of 2 g (4.25 mmol) of 2-(10,10-dimethyl-10H-indeno[2,1-b]triphenylen-6-yl)-4,4,5,5-tetramethyl-1,3,2-dioxaborolane, 3 g (4.68 mmol) of N-(4-bromophenyl)-N-(4-(9-phenyl-9H-carbazol-3-yl) phenyl)biphenyl-4-amine, 0.05 g (0.04 mmol) of Pd(PPh$_3$)$_4$, 4.25 ml of 2M Na$_2$CO$_3$, 10 ml of EtOH and 30 ml toluene was degassed and placed under nitrogen, and then heated at 100° C. overnight. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (2.38 g, 2.64 mmol, 62%) as a white solid. 1H NMR (CDCl3, 400 MHz): chemical shift (ppm) 9.05~8.91 (m, 3H), 8.38~8.18 (m, 6H), 7.92~7.77 (m, 6H), 7.68~7.49 (m, 14H), 7.41~7.27 (m, 7H), 6.84~6.68 (m, 6H), 1.78 (s, 6H). MS (m/z, FAB$^+$): 905.6

Example 8

Synthesis of EX27

Synthesis of N-(triphenyl-4-yl)-N-(4-(10,10-dimethyl-10H-indeno[2,1-b]triphenylen-6-yl)phenyl) dibenzo[b,d]furan-3-amine

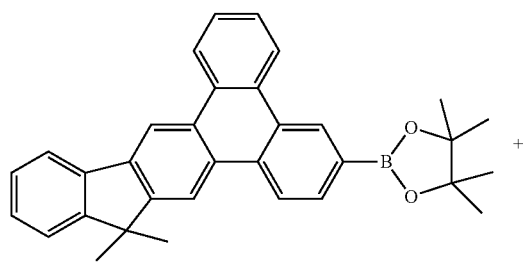

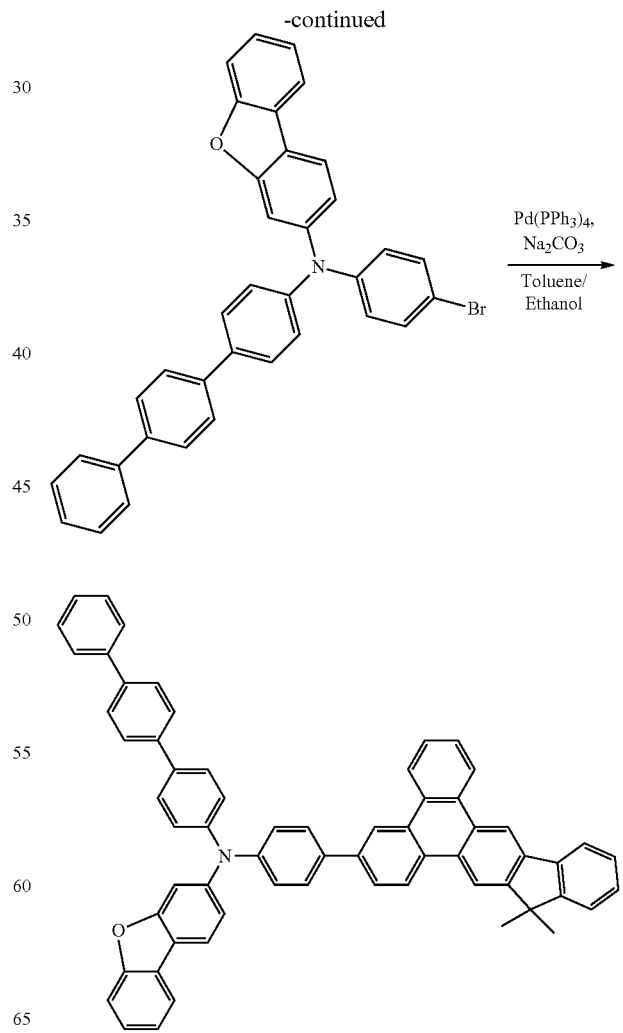

N-(triphenyl-4-yl)-N-(4-bromophenyl)dibenzo[b,d]furan-3-amine instead of N-(4-bromophenyl)-N-(4-(9-phenyl-9H-carbazol-3-yl) phenyl) biphenyl-4-amine, except for using the same method as in synthesis example 7, the desired compound of N-(triphenyl-4-yl)-N-(4-(10,10-dimethyl-10H-indeno[2,1-b]triphenylen-6-yl)phenyl)dibenzo[b,d]furan-3-amine (2.15 g, yield=67%) was obtained. MS (m/z, FAB+): 753.4

Example 9

Synthesis of EX29

Synthesis of N-(4-(dibenzo[b,d]furan-4-yl)phenyl)-N-(4'-(10, 10-dimethyl-10H-indeno[2,1-b]triphenylen-6-yl)biphenyl-4-yl)biphenyl-4-amine

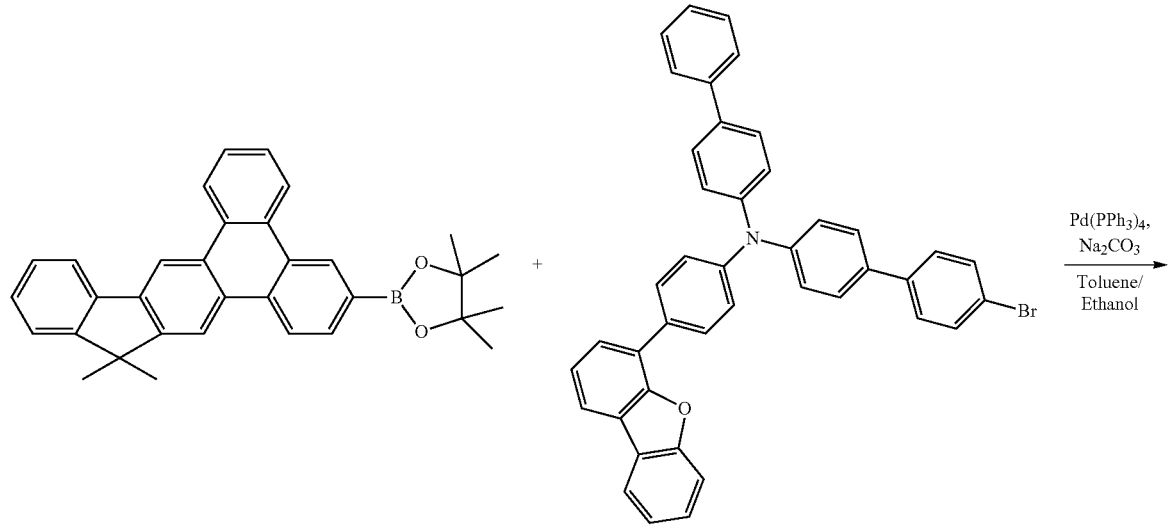

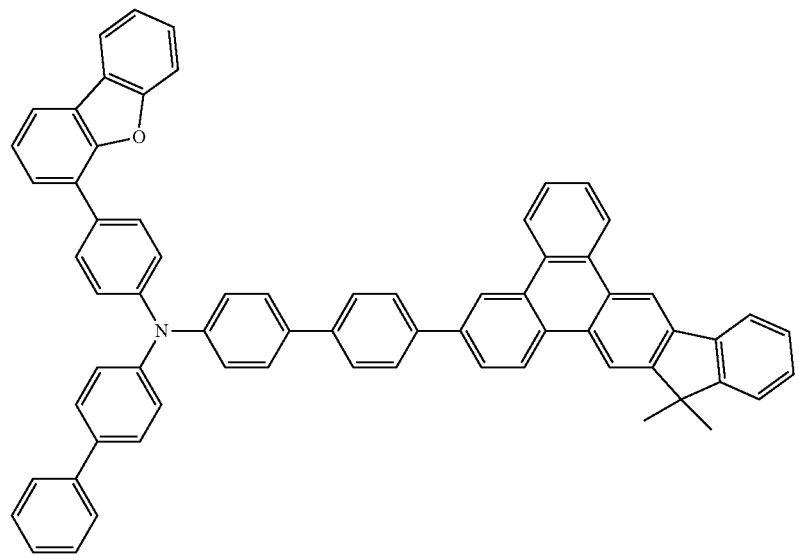

N-(4'-bromobiphenyl-4-yl)-N-(4-(dibenzo[b,d]furan-4-yl) phenyl)biphenyl-4-amine instead of N-(4-bromophenyl)-N-(4-(9-phenyl-9H-carbazol-3-yl)phenyl) biphenyl-4-amine, except for using the same method as in synthesis example 7, the desired compound of N-(4-(dibenzo[b,d]furan-4-yl) phenyl)-N-(4'-(10,10-dimethyl-10H-indeno[2,1-b]triphenylen-6-yl)biphenyl-4-yl)biphenyl-4-amine (2.43 g, yield=63%) was obtained. MS (m/z, FAB+): 906.7

Example 10

Synthesis of EX31

Synthesis of N,N-bis(4-(dibenzo[b,d]furan-4-yl)phenyl)-4'-(10,10-dimethyl-10H-indeno[2,1-b]triphenylen-6-yl)biphenyl-4-amine

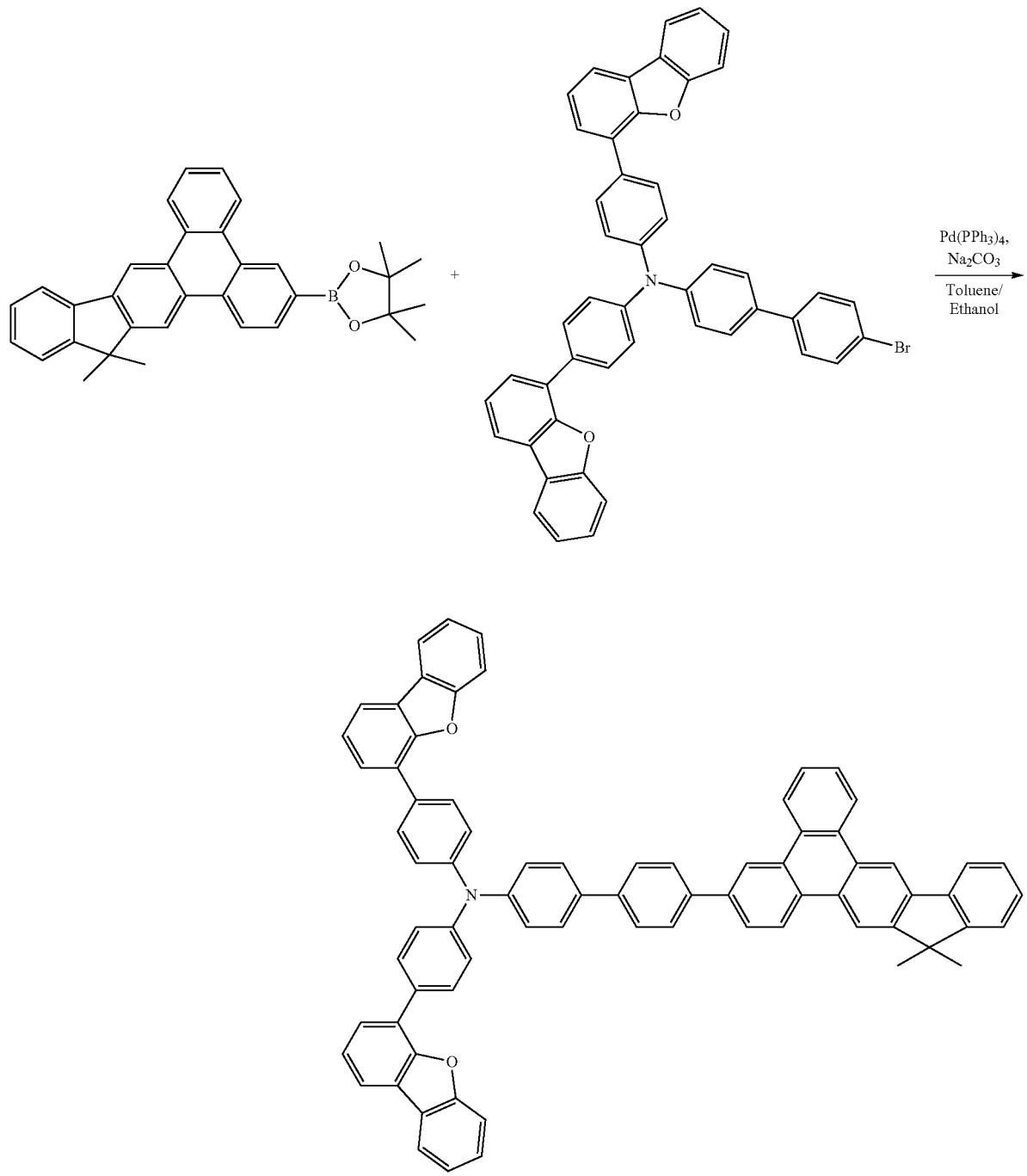

4'-bromo-N,N-bis(4-(dibenzo[b, d]furan-4-yl)phenyl)biphenyl-4-amine instead of N-(4-bromophenyl)-N-(4-(9-phenyl-9H-carbazol-3-yl) phenyl) biphenyl-4-amine, except for using the same method as in synthesis example 7, the desired compound of N,N-bis(4-(dibenzo[b,d]furan-4-yl)phenyl)-4'-(10,10-dimethyl-10H-indeno[2,1-b]triphenylen-6-yl)biphenyl-4-amine (2.58 g, yield=61%) was obtained. MS (m/z, FAB$^+$): 996.4

General Method of Producing Organic El Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f: 2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine(NPB) is most widely used as the hole transporting layer. 10,10-dimethyl-12-(10-(3-(naphthalene-2-yl)phenyl) anthracen-9-yl)-10H-indeno[2,1-b]triphenylene (BH) is used as blue emitting host in organic EL device, and N1,N1,N6,N6-tetram-tolylpyrene-1,6-diamine (D1) is used as blue guest. 2-(10,10-dimethyl-10H-indeno[2,1-b]triphenylen-13-yl)-4,6-bis-5-phenylbiphenyl-3-yl)-1,3,5-triazine(ET3) is used as electron transporting material to co-deposit with 8-hydroxyquinolato-lithium(LiQ) in organic EL device. Tris(2-phenylpyridinato)iridium(III)(D2) is used as phosphorescent dopant. H2 (see the below chemical structure) is used as phosphorescent host for organic EL device. The prior art of OLED materials for producing standard organic EL device control and comparable material in this invention shown its chemical structure as following structure:

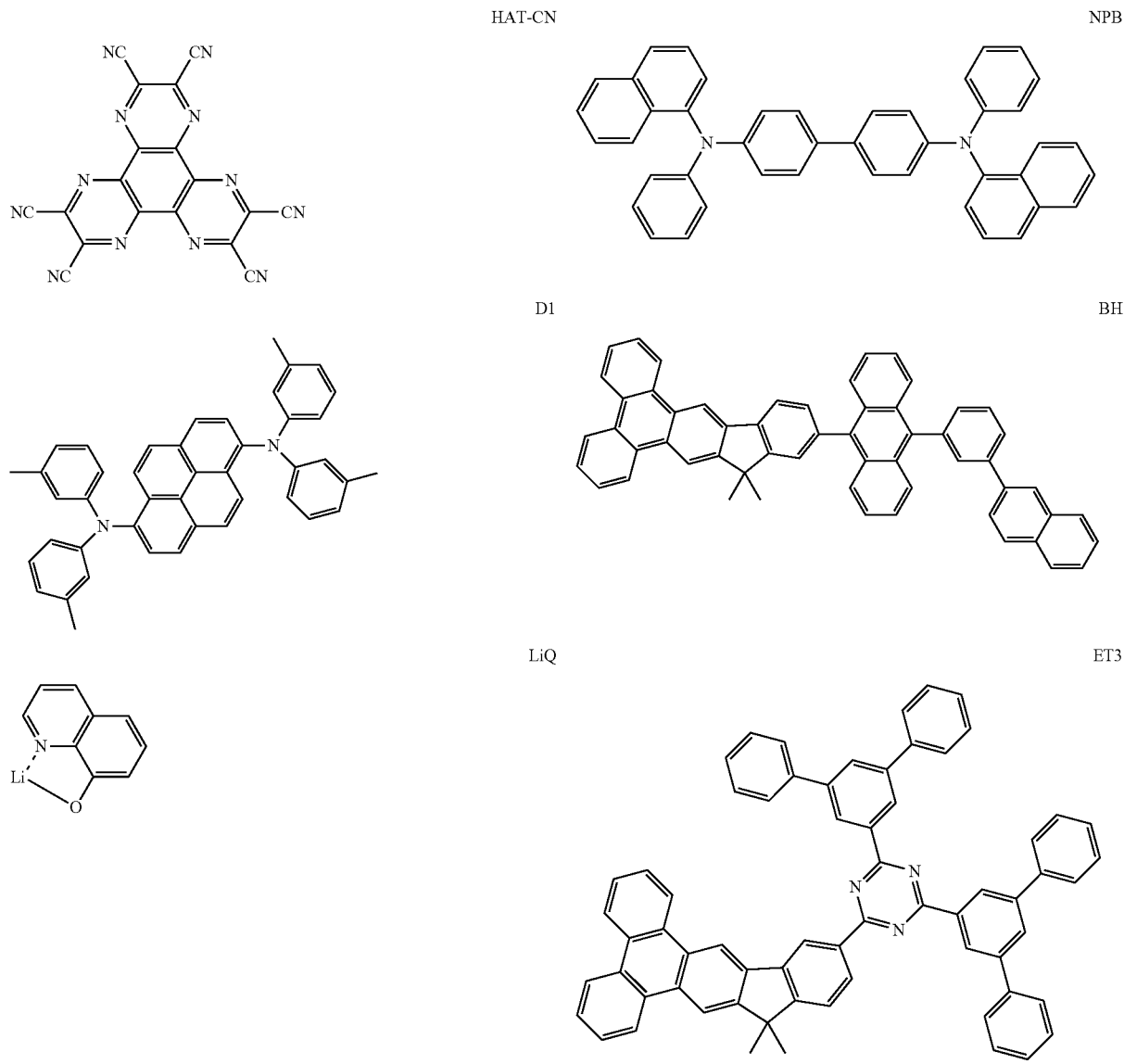

H2
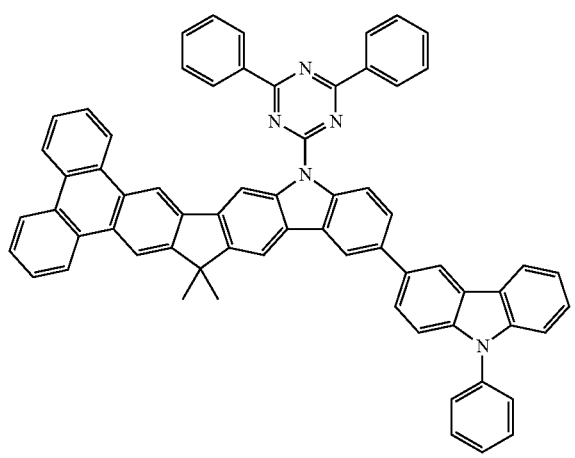
D2
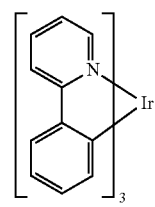
EX2
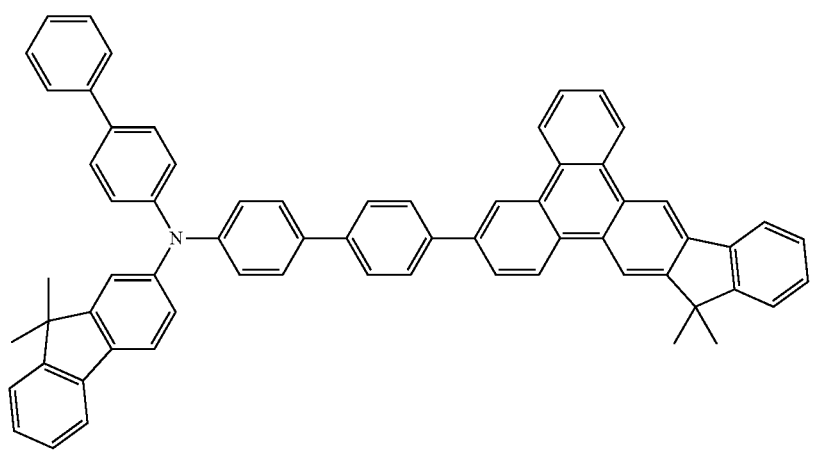
EX3
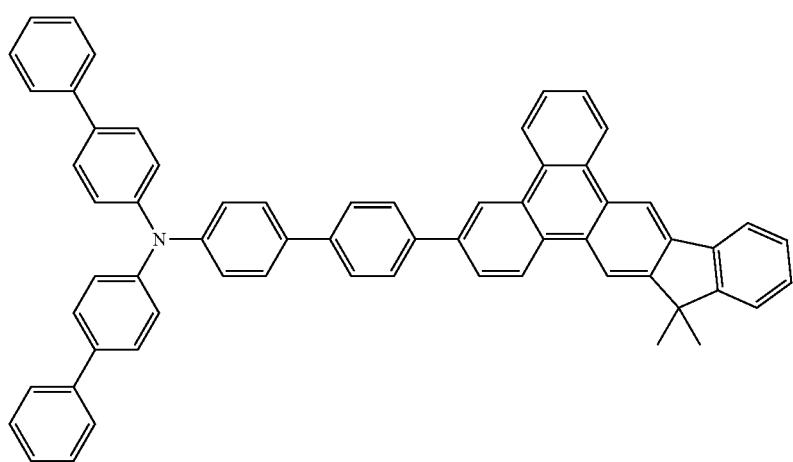

EX8
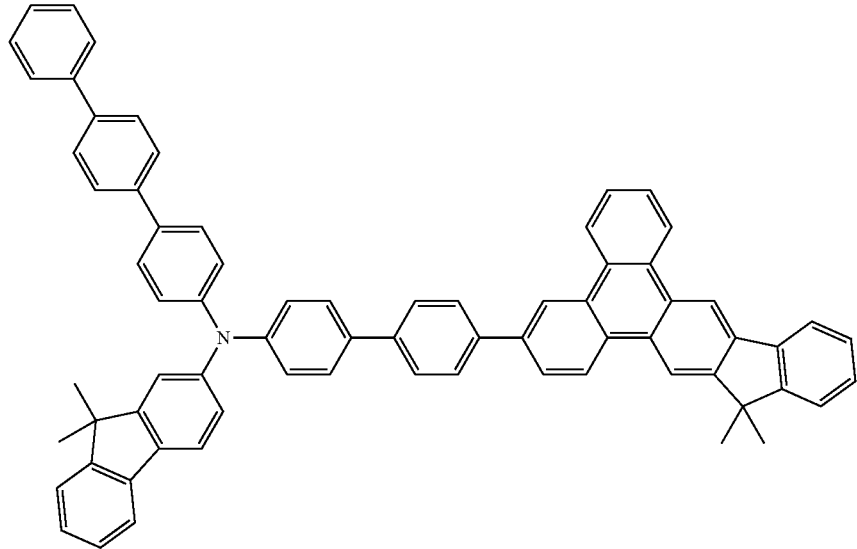
EX11
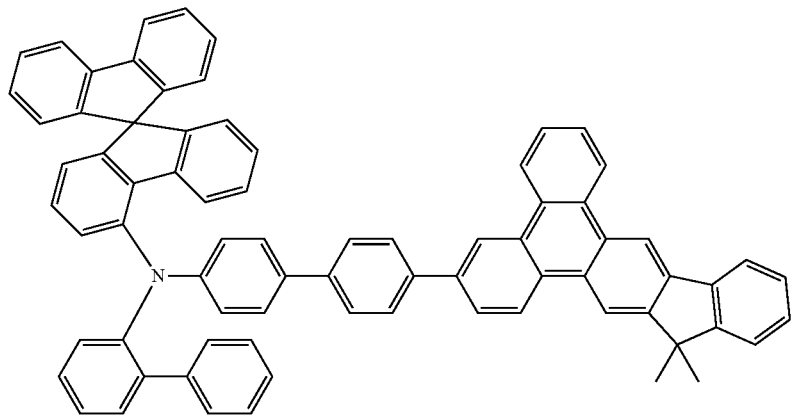
EX12
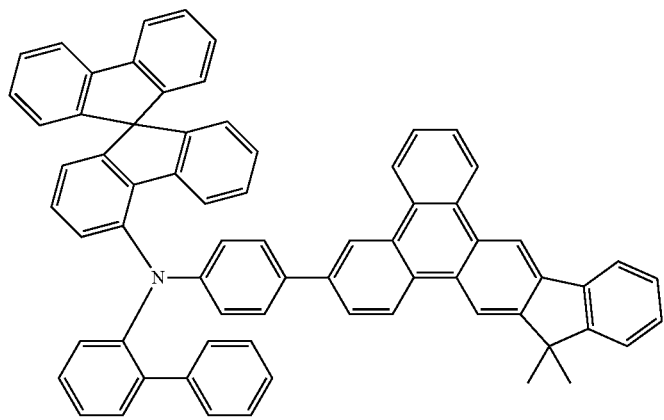

EX15
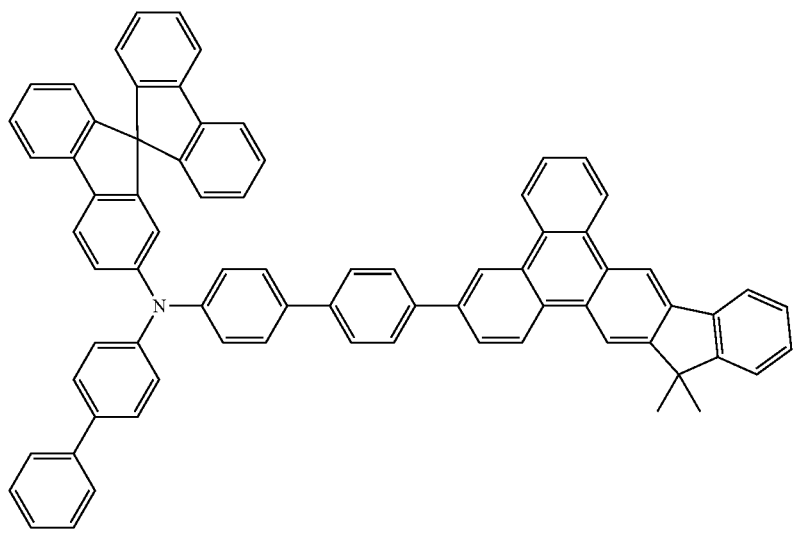
EX22
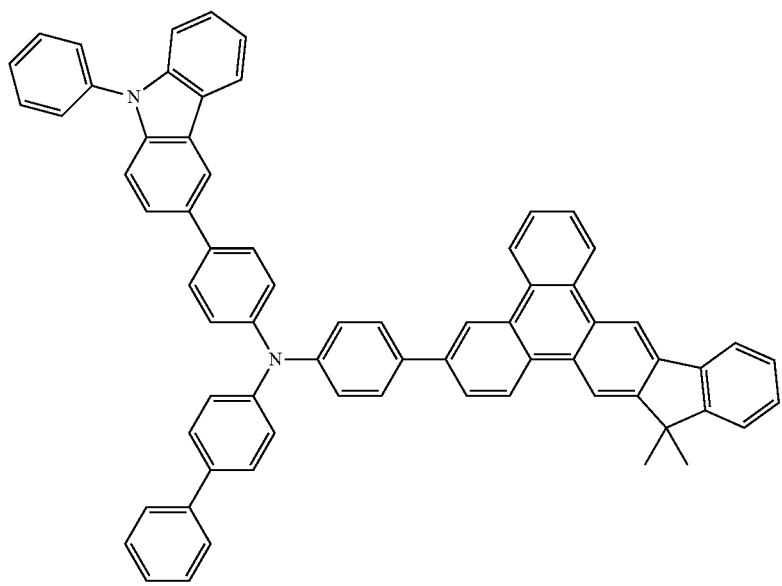

EX27
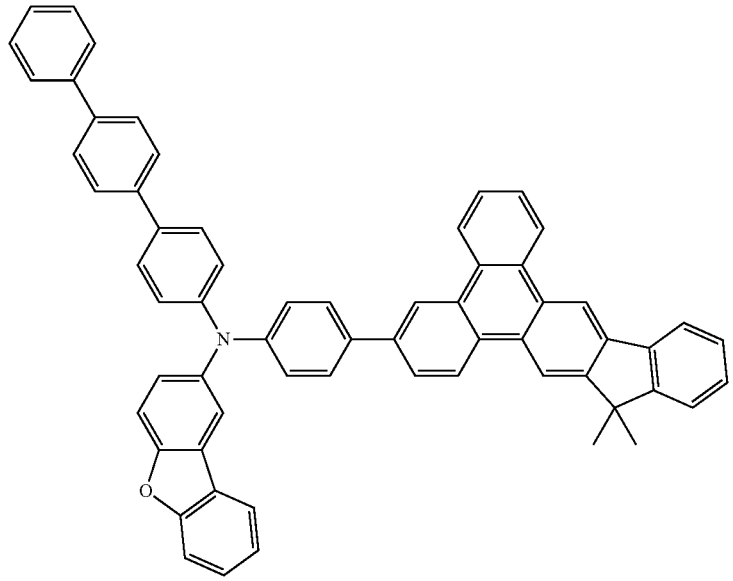
EX29
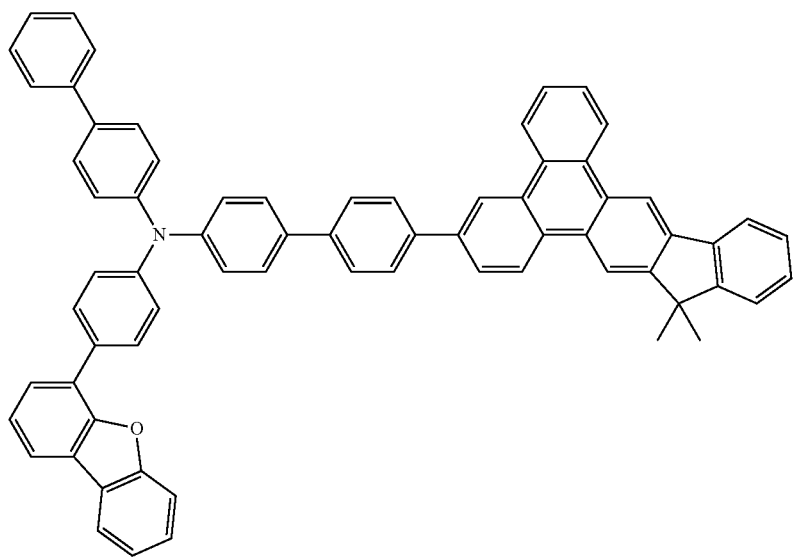

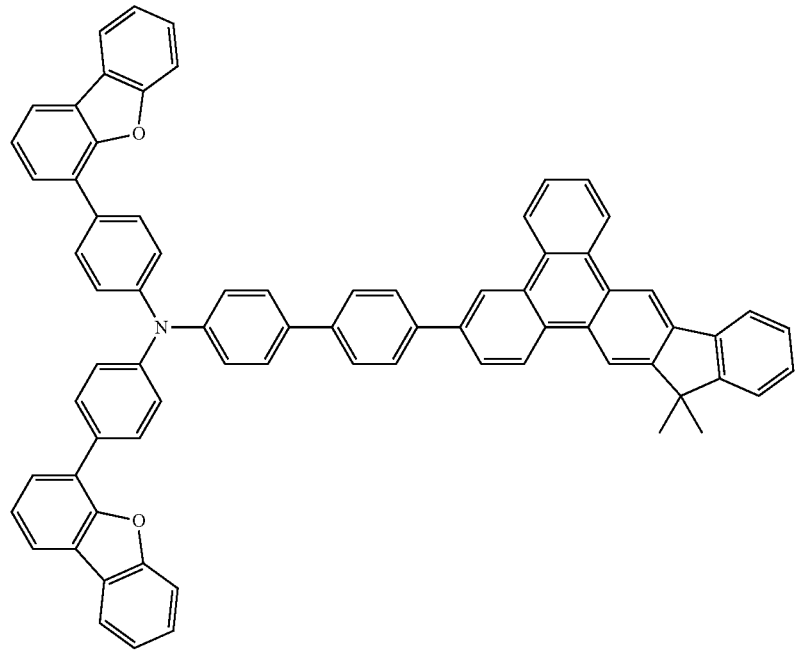

EX31

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 11

Using a procedure analogous to the above mentioned general method, fluorescent blue-emitting organic EL device having the following device structure I was produced (See FIG. 1). Device I: ITO/HAT-CN (20 nm)/hole transport material (HTM)(110 nm)/electron blocking material (EBM)(5 nm)/BH doped 5% D1 (30 nm)/ET3 co-deposit 50% LiQ (40 nm)/LiQ (1 nm)/Al (160 nm). The I-V-B (at 1000 nits) and half-life time of fluorescent blue-emitting organic EL device testing report as Table 1. The half-life time is defined that the initial luminance of 1000 cd/m² has dropped to half.

TABLE 1

| HTM | EBM | Voltage (V) | Efficiency (cd/A) | CIE(y) | Half-life time (hour) |
|---|---|---|---|---|---|
| NPB | — | 5.5 | 4.5 | 0.173 | 180 |
| EX2 | — | 5.2 | 5.0 | 0.178 | 260 |

TABLE 1-continued

| HTM | EBM | Voltage (V) | Efficiency (cd/A) | CIE(y) | Half-life time (hour) |
|---|---|---|---|---|---|
| EX3 | — | 5.0 | 5.1 | 0.178 | 350 |
| NPB | EX8 | 5.6 | 5.6 | 0.180 | 380 |
| NPB | EX11 | 5.8 | 5.8 | 0.179 | 350 |
| NPB | EX12 | 5.5 | 6.4 | 0.180 | 280 |
| NPB | EX15 | 6.0 | 5.1 | 0.181 | 450 |
| NPB | EX22 | 5.8 | 5.6 | 0.180 | 480 |
| NPB | EX27 | 5.6 | 5.0 | 0.178 | 280 |
| NPB | EX29 | 5.4 | 5.3 | 0.179 | 380 |
| NPB | EX31 | 6.2 | 4.6 | 0.180 | 400 |
| EX2 | EX12 | 4.8 | 6.5 | 0.183 | 490 |
| EX3 | EX11 | 4.7 | 6.0 | 0.182 | 500 |
| EX3 | EX12 | 4.5 | 6.3 | 0.183 | 460 |

Example 12

Using a procedure analogous to the above mentioned general method, phosphorescent emitting organic EL device having the following device structures are produced (See FIG. 1): Device I: ITO/HAT-CN (20 nm)/hole transport material (HTM)(110 nm)/electron blocking material (EBM)(5 nm)/H2 doped 12% D2(35 nm)/ET3 co-deposit 50% LiQ(40 nm)/LiQ(1 nm)/Al (160 nm). The I-V-B (at 1000 nits) and half-life time of phosphorescent emitting organic EL device testing report as Table 2. The half-life time is defined that the initial luminance of 3000 cd/m² has dropped to half.

TABLE 2

| HTM | EBM | Voltage (V) | Efficiency (cd/A) | CIE(x, y) | Half-life time (hour) |
|---|---|---|---|---|---|
| NPB | — | 3.8 | 32 | 0.342, 0.605 | 620 |
| EX2 | — | 3.5 | 36 | 0.353, 0.603 | 810 |
| EX3 | — | 3.6 | 34 | 0.354, 0.604 | 750 |

TABLE 2-continued

| HTM | EBM | Voltage (V) | Efficiency (cd/A) | CIE(x, y) | Half-life time (hour) |
|---|---|---|---|---|---|
| NPB | EX8 | 4.8 | 35 | 0.362, 0.610 | 860 |
| NPB | EX11 | 4.3 | 38 | 0.361, 0.612 | 1030 |
| NPB | EX12 | 4.5 | 41 | 0.360, 0.610 | 1040 |
| NPB | EX15 | 4.5 | 36 | 0.360, 0.612 | 1100 |
| NPB | EX22 | 4.6 | 33 | 0.361, 0.610 | 900 |
| NPB | EX27 | 4.8 | 28 | 0.359, 0.611 | 820 |
| NPB | EX29 | 4.6 | 35 | 0.361, 0.611 | 900 |
| NPB | EX31 | 5.0 | 29 | 0.360, 0.610 | 950 |
| EX2 | EX12 | 4.8 | 40 | 0.368, 0.617 | 1200 |
| EX2 | EX11 | 4.5 | 42 | 0.368, 0.616 | 1350 |
| EX3 | EX12 | 4.3 | 38 | 0.369, 0.618 | 1250 |

In the above preferred embodiments for organic EL device test report (see Table 1 and Table 2), we show that with a general formula (I) in the present invention display good performance and shown higher efficiency and longer half-life time.

To sum up, the present invention discloses a indenotriphenylene-based amine derivative which can be used for organic EL device is disclosed. More specifically, an organic EL device employing the derivative as hole transport material, electron blocking material. The mentioned compound are represented by the following formula (I):

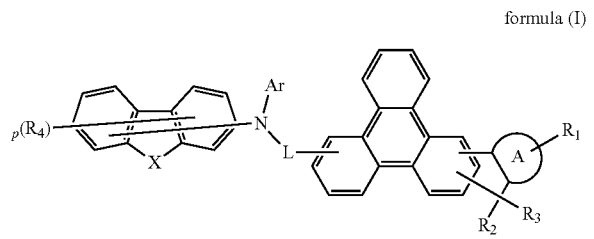

formula (I)

wherein A ring represents a phenyl group and fused ring hydrocarbon units with two to four rings group, L represents a single bond or a substituted or unsubstituted divalent arylene group having 6 to 30 ring carbon atoms, p represents an integer of 0 to 7, X represents a divalent bridge selected from the atom or group consisting from O, S, $C(R_5)(R_6)$ and $NR_7$ or represents non-bridge and to form as a substituted or unsubstituted biphenyl group; Ar is selected from the group consisting of a substituted or unsubstituted aryl group having 6 to 50 carbon atoms, a substituted or unsubstituted heteroaryl group having 3 to 50 carbon atoms, $R_1$ to $R_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. An indenotriphenylene-based amine derivative represented by the following formula (I):

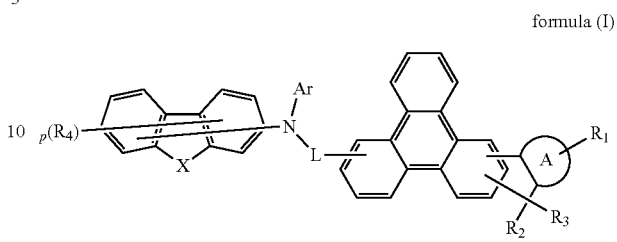

formula (I)

wherein ring A represents a phenyl group or a fused ring hydrocarbon units with two to four rings, L represents a single bond or a substituted or unsubstituted divalent arylene group having 6 to 30 ring carbon atoms, p represents an integer of 0 to 7, X is absent or represents a divalent bridge selected from the atom or group consisting from O, S, $C(R_5)(R_6)$ and $NR_7$; Ar is a substituted or unsubstituted aryl group having 6 to 50 carbon atoms, or a substituted or unsubstituted heteroaryl group having 3 to 50 carbon atoms, $R_1$ to $R_7$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The indenotriphenylene-based amine derivative according to claim 1, wherein L is selected from the group consisting of groups represented as following formulas:

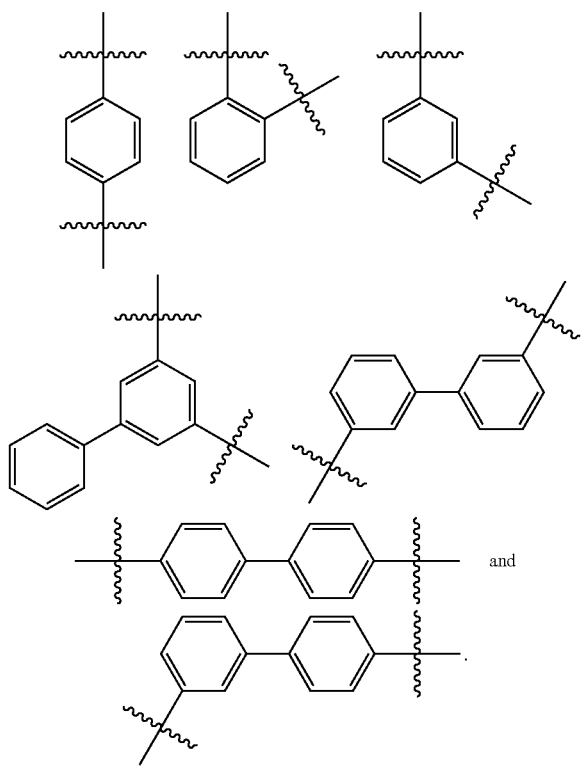

3. The indenotriphenylene-based amine derivative according to claim 1, wherein the ring A is selected from the group consisting of naphthyl group, anthracenyl group, phenanthrenyl group, pyrenyl group, chrysenyl group and triphenylene group.

4. The indenotriphenylene-based amine derivative according to claim 1, wherein Ar is selected from the group consisting of the following formulas:

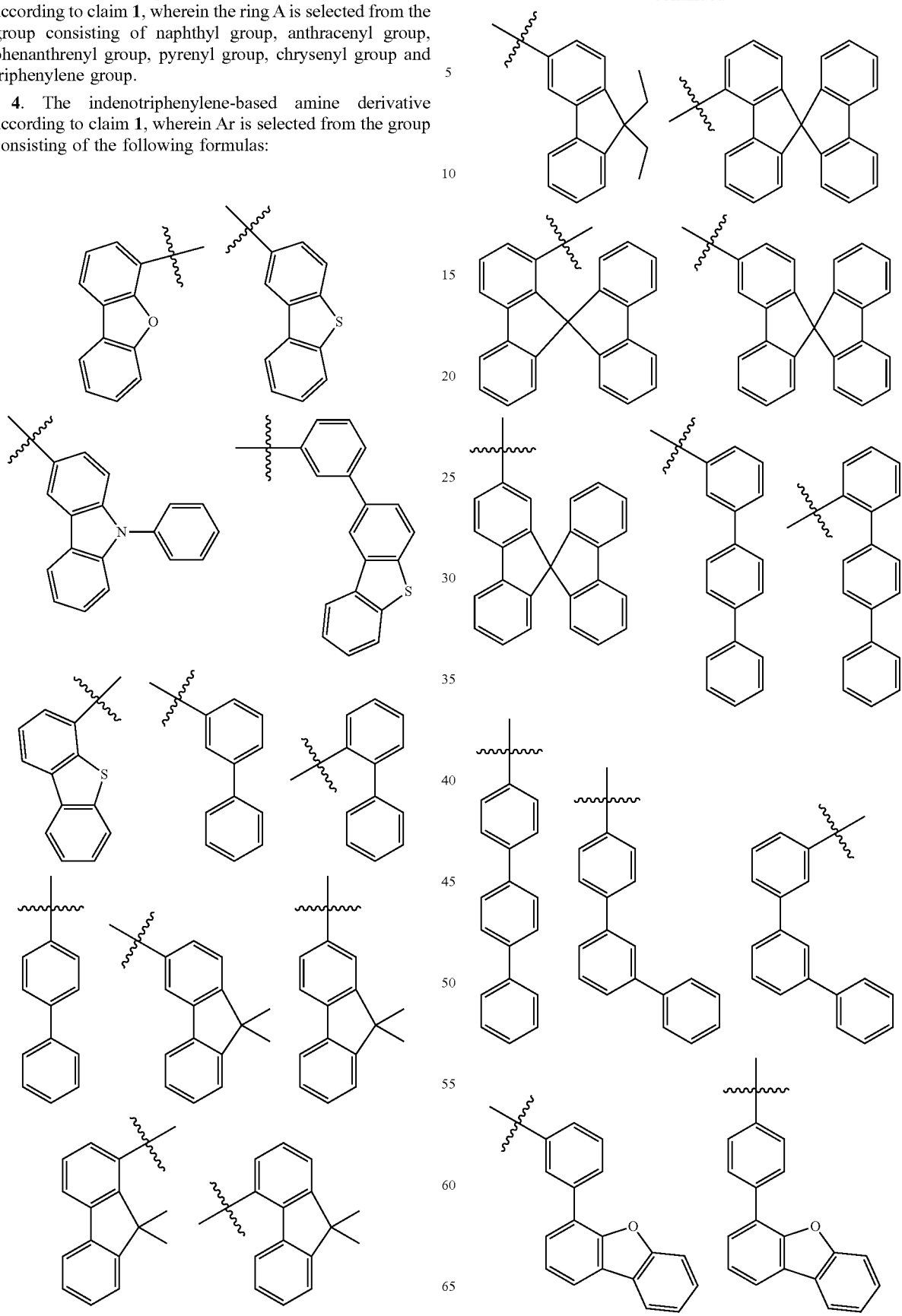

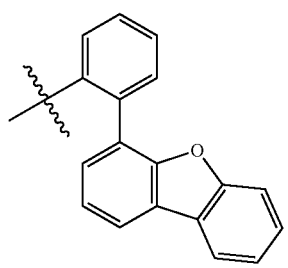 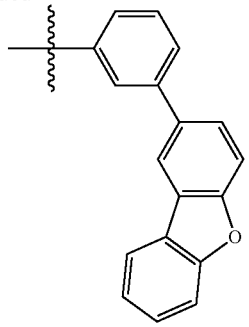 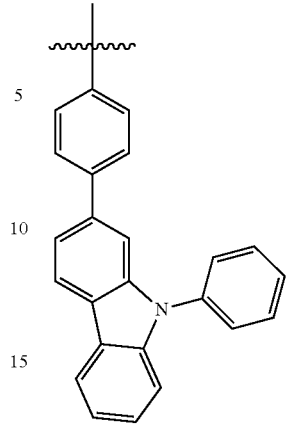 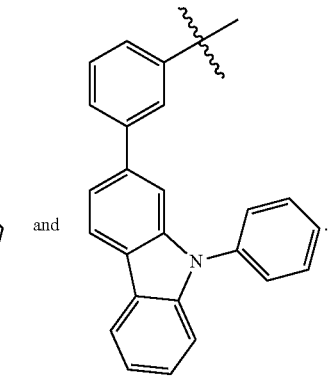

5. An organic electroluminescence device comprising a pair of electrodes consisting of a cathode and an anode, and a light emitting layer and one or more organic thin film layers between the pair of electrodes, wherein one or more organic thin film layers comprise the indenotriphenylene-based amine derivative according to claim 1.

6. The organic electroluminescence device according to claim 5, wherein the organic thin film layer comprising the indenotriphenylene-based amine derivative with formula (I) is a hole transport layer.

7. The organic electroluminescence device according to claim 5, wherein the organic thin film layer comprising the indenotriphenylene-based amine derivative with formula (I) is an electron blocking layer.

8. The indenotriphenylene-based amine derivative according to claim 1, wherein the indenotriphenylene-based amine derivative is selected from the group consisting of:

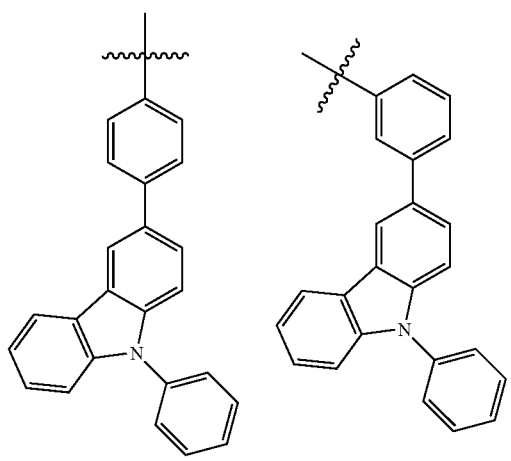

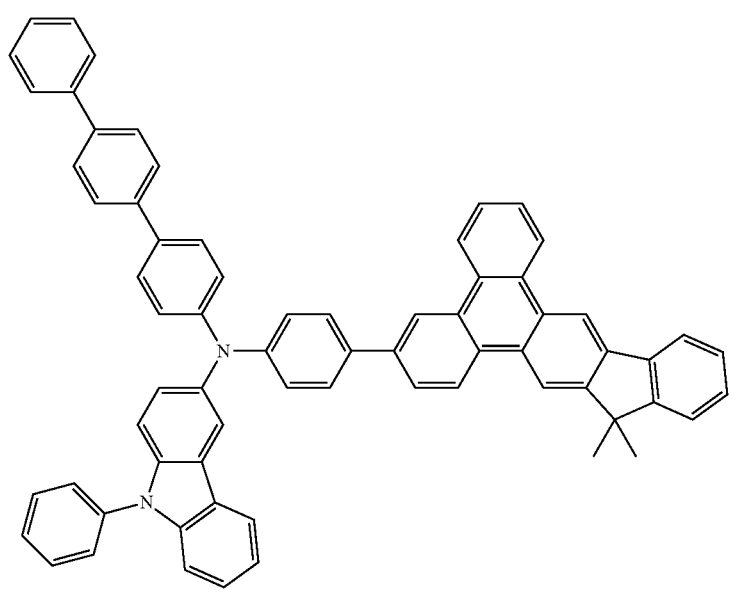

EX1

-continued
EX2
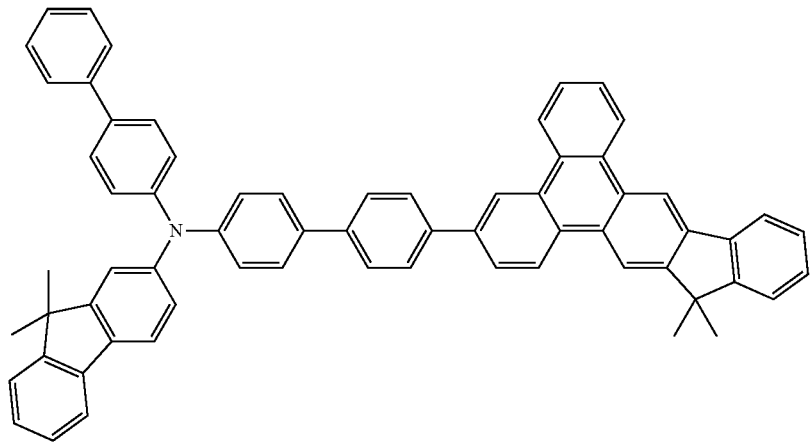
EX3
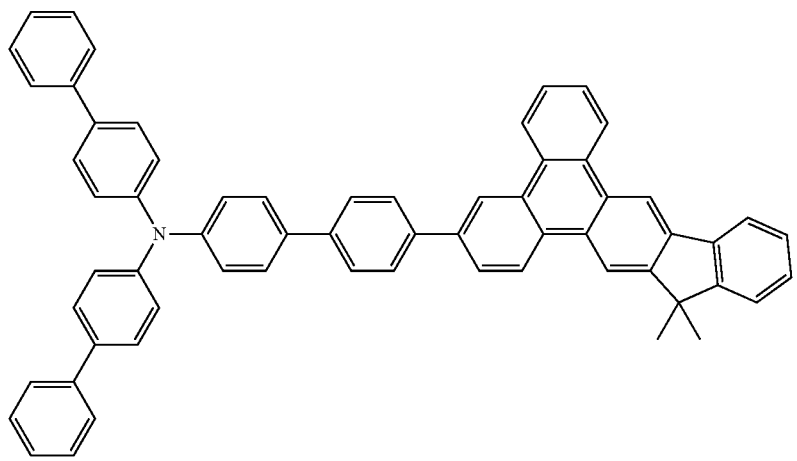
EX4
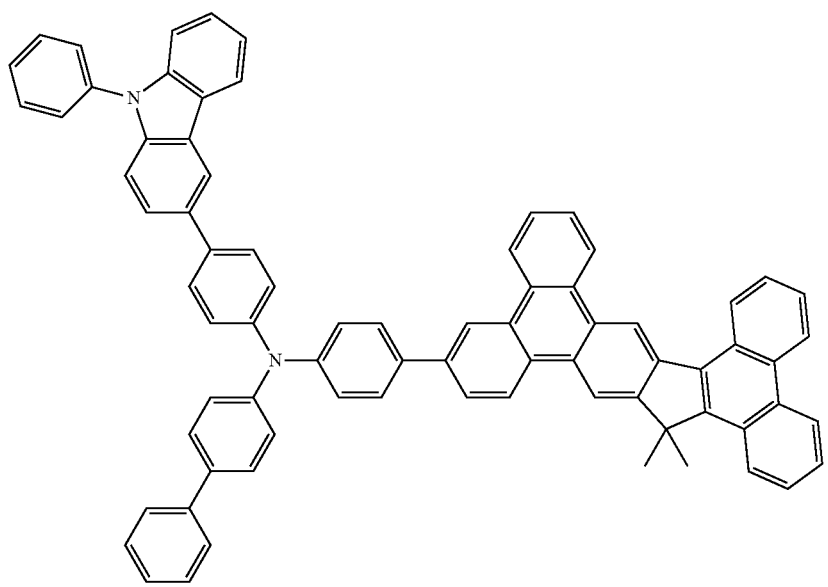

-continued
EX5
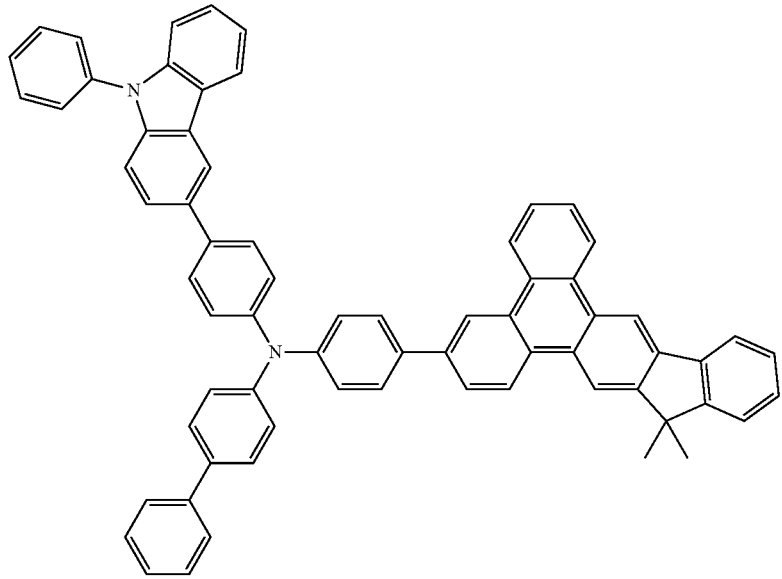
EX6
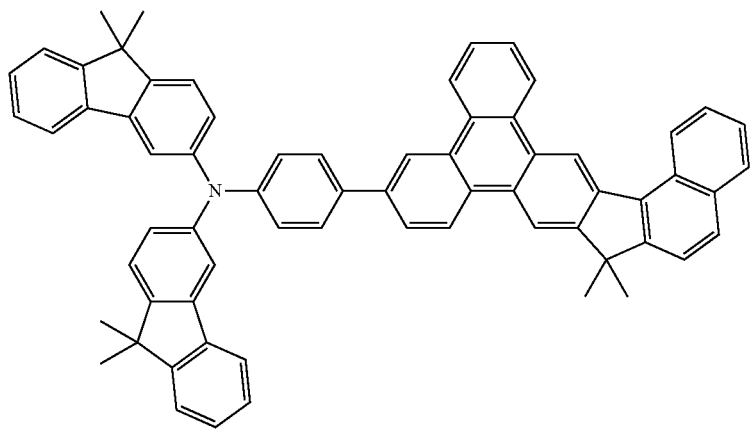
EX7
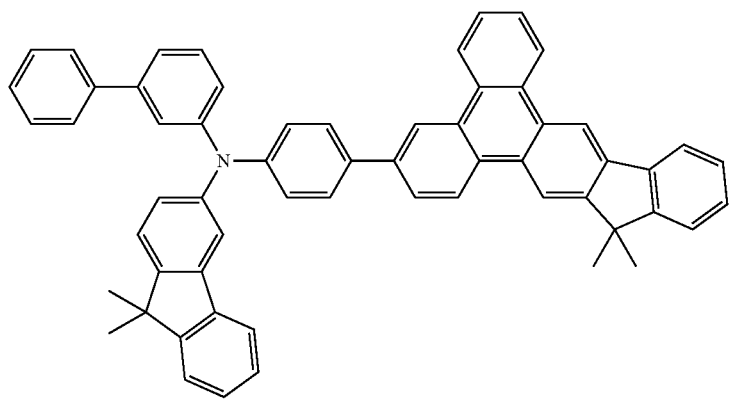

-continued
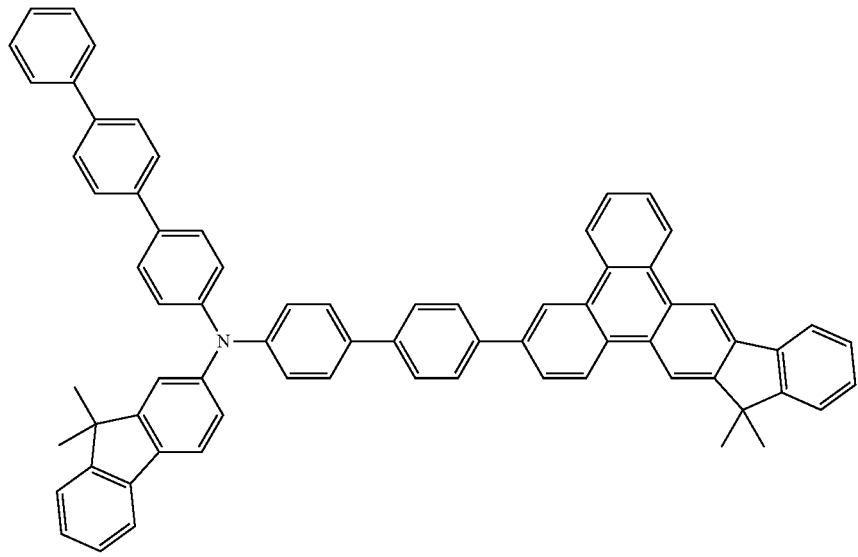
EX8
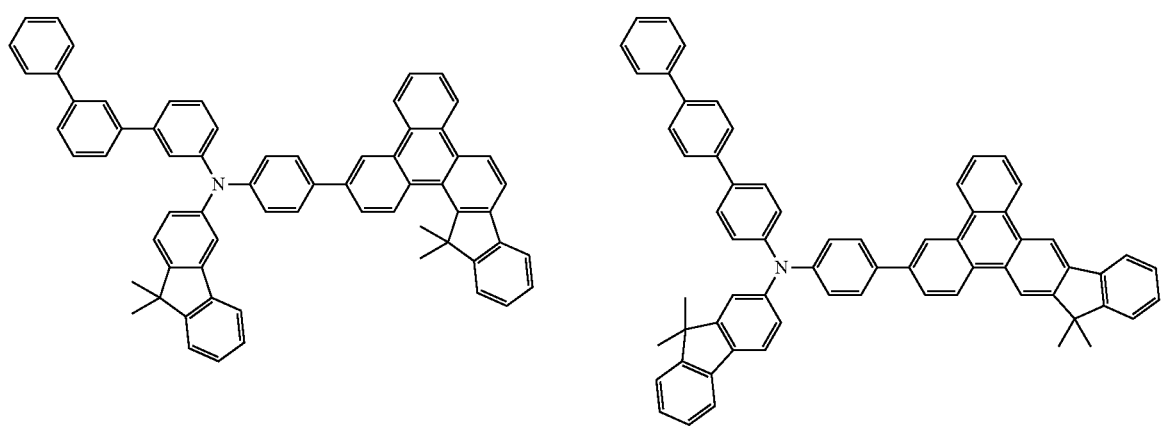
EX9  EX10
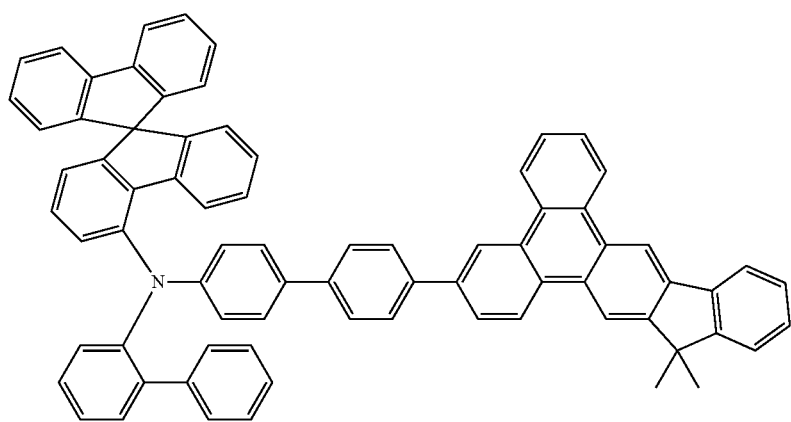
EX11

EX12
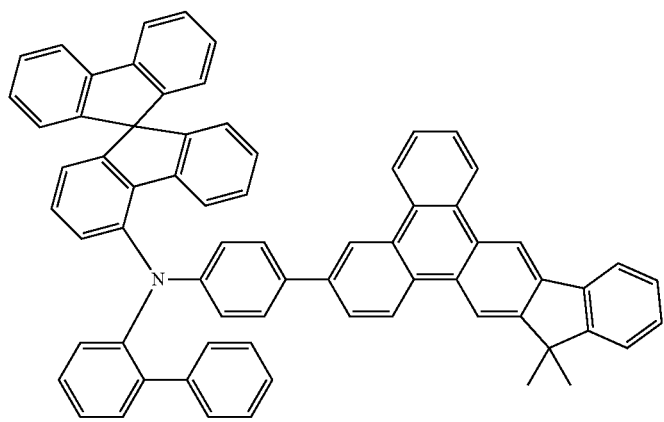
EX13
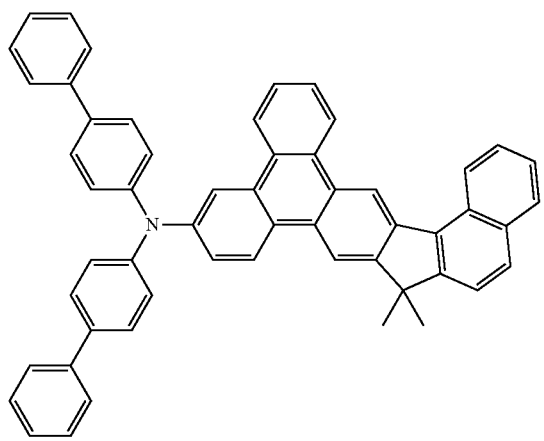
EX14
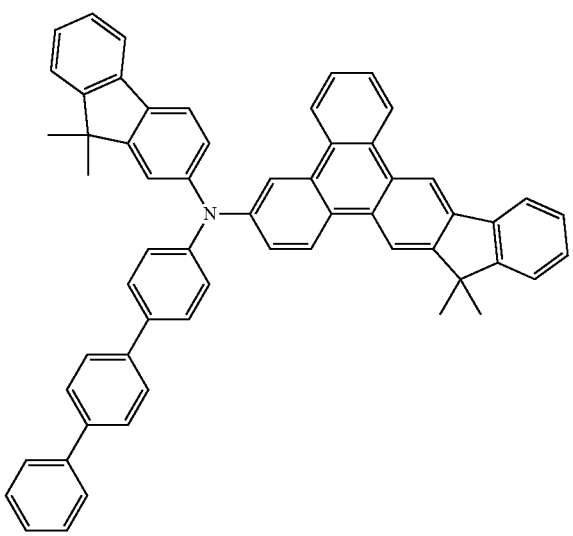
EX15
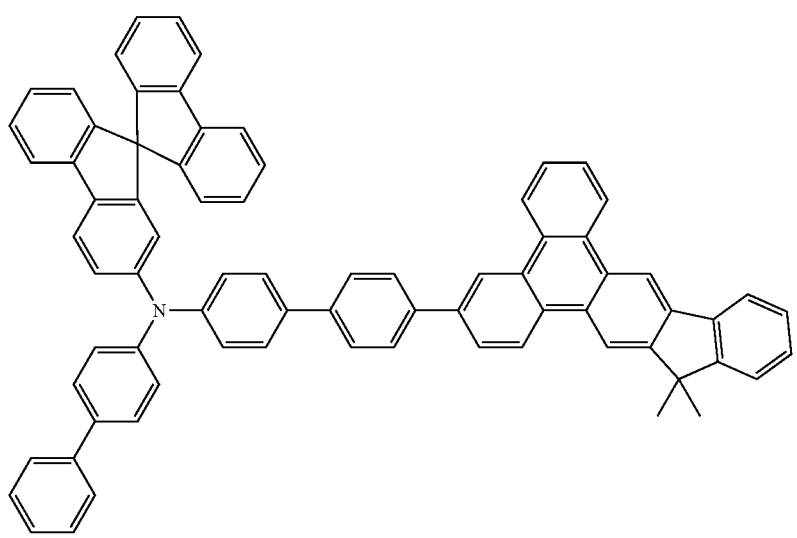

EX16
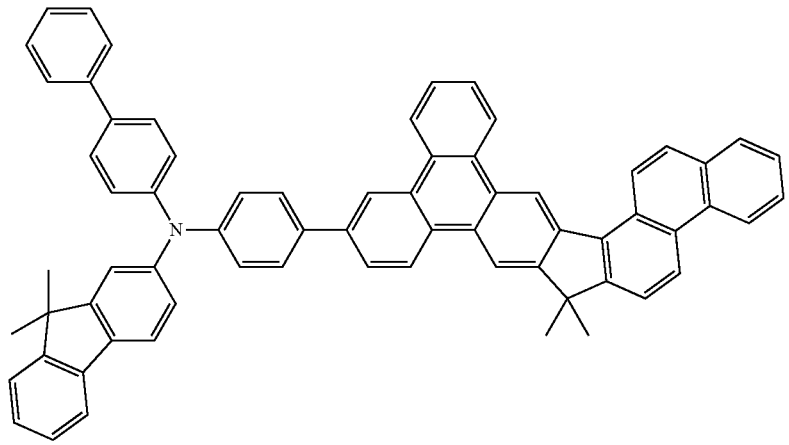
EX17
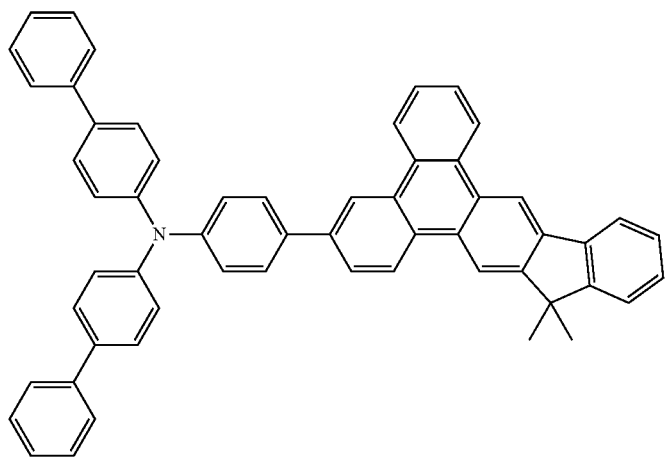
EX18
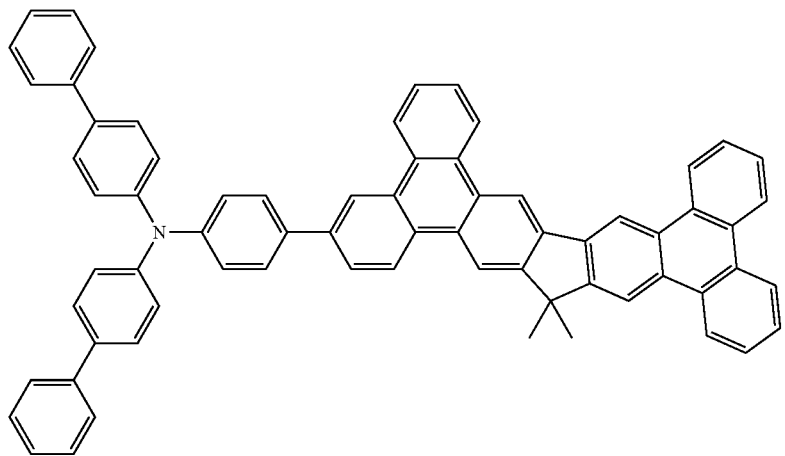

-continued
EX19
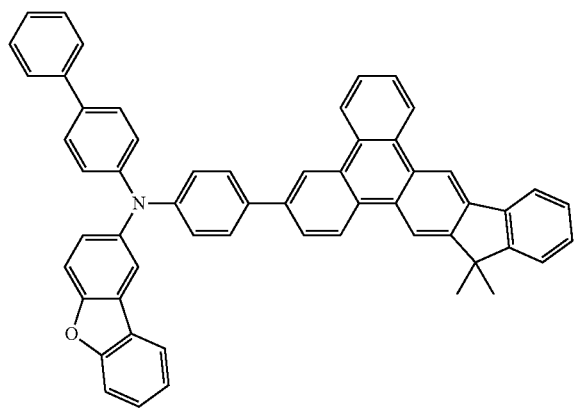
EX20
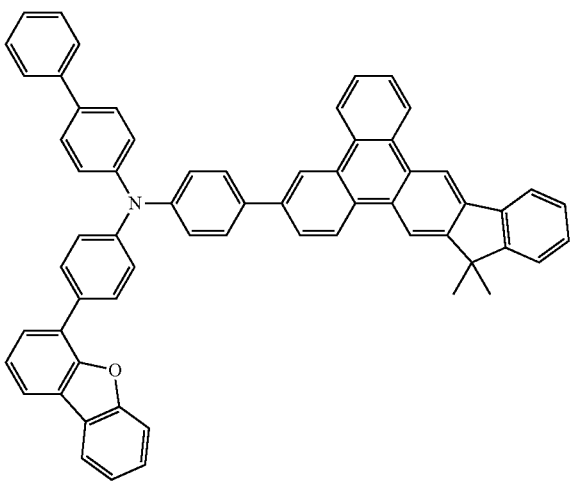
EX21
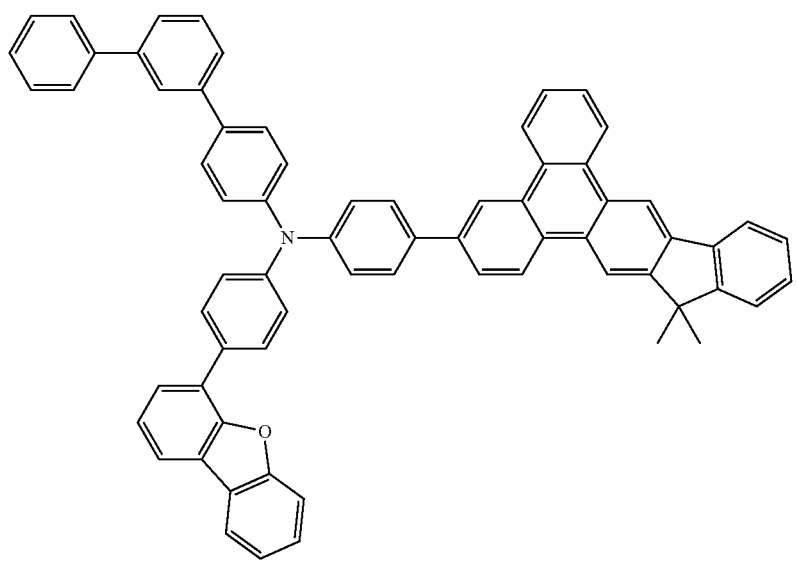
EX22
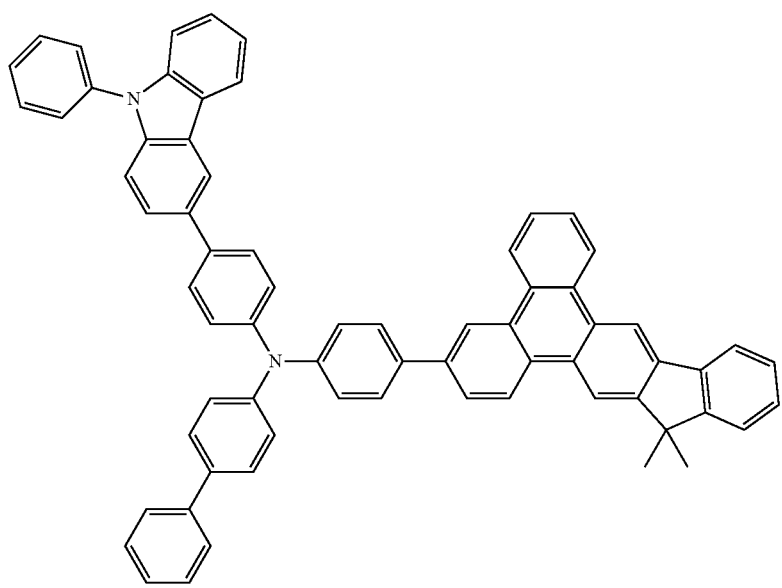

-continued
EX23
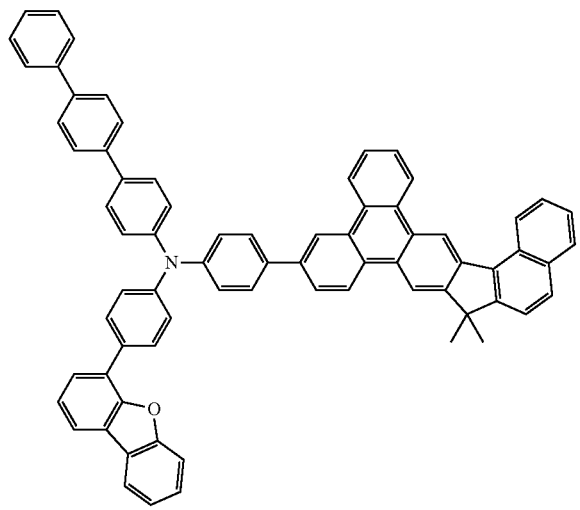
EX24
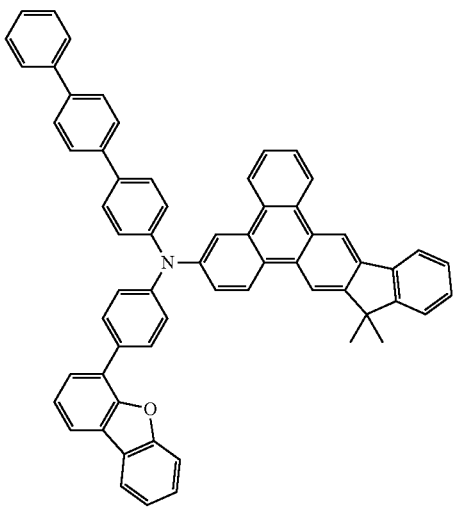
EX25
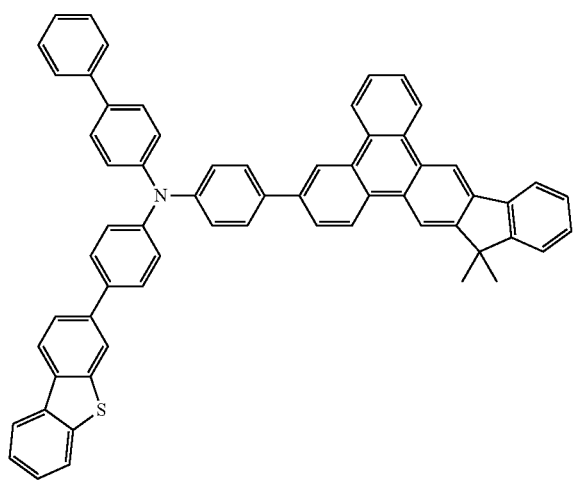
EX26
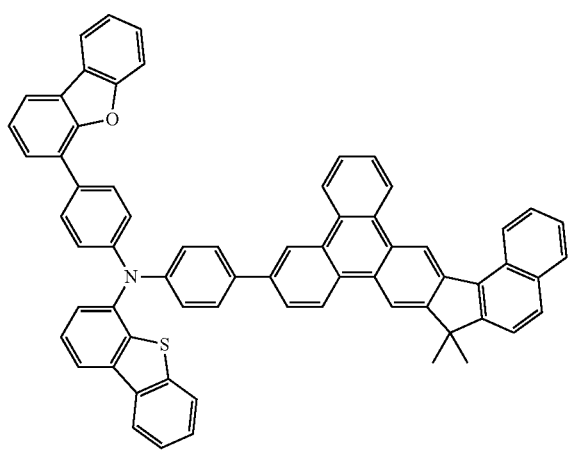
EX27
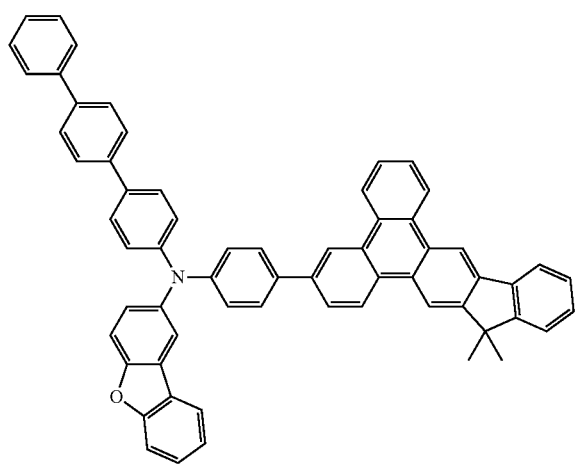
EX28
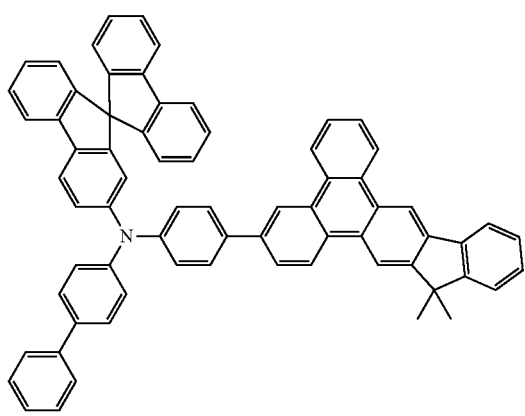

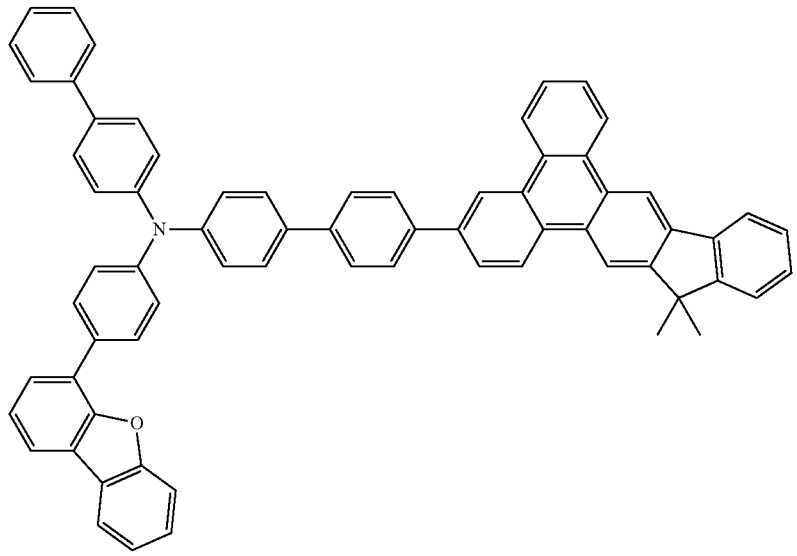
EX29
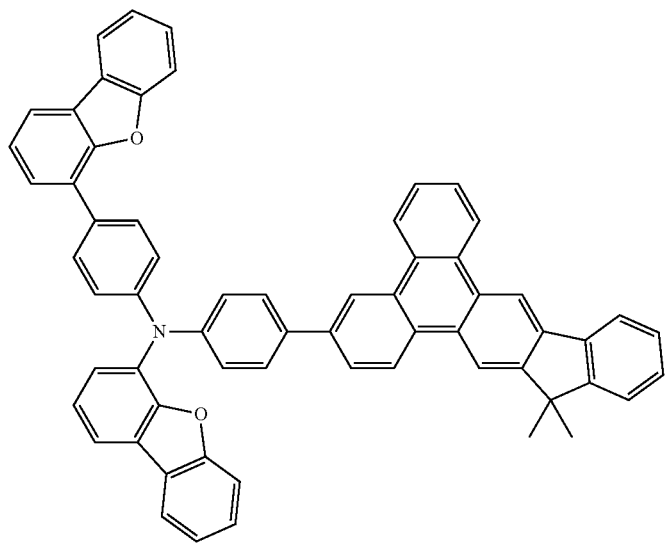
EX30

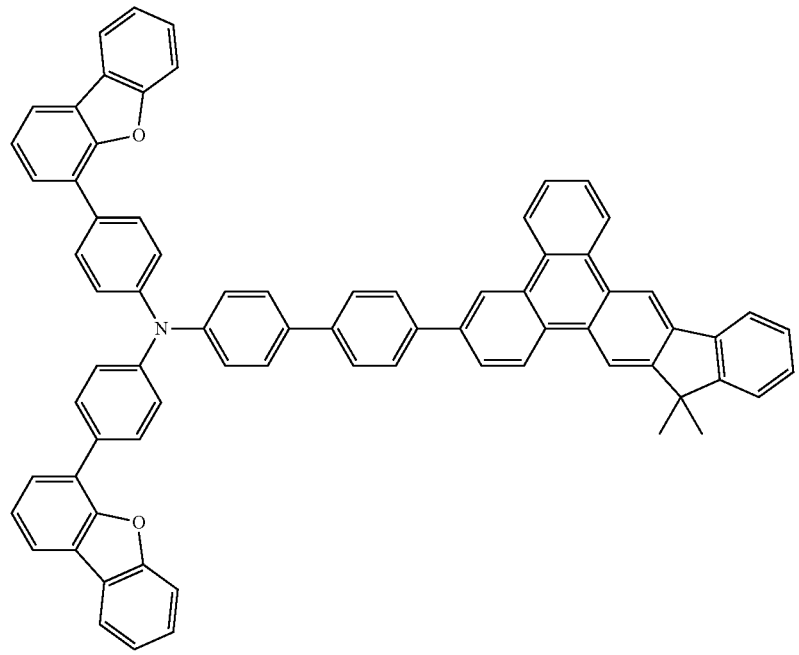
EX31
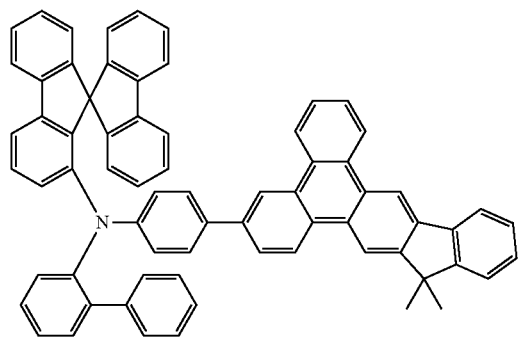
EX32
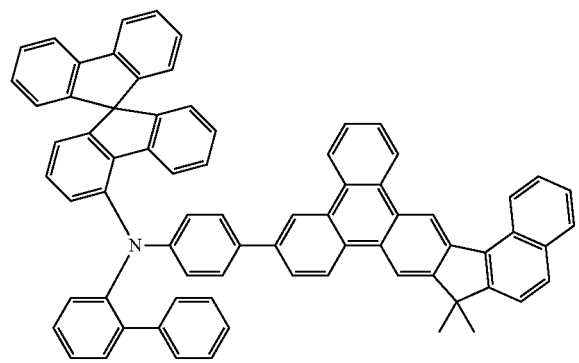
EX33
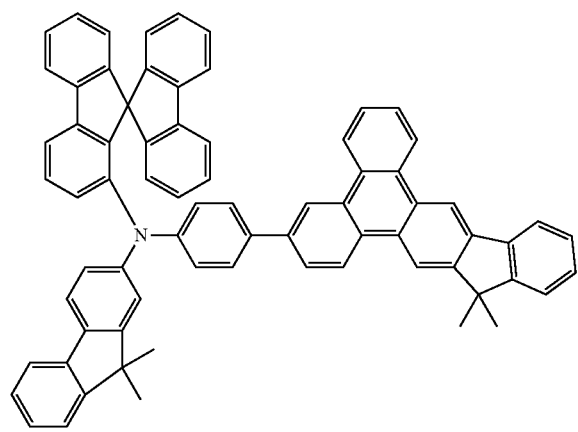
EX34
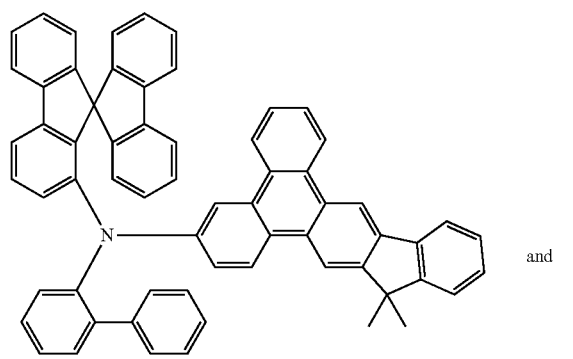
EX35
and EX36
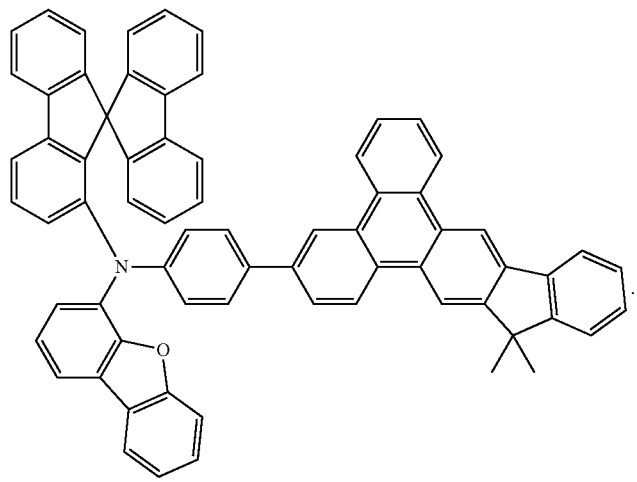
* * * * *